US011204358B2

(12) United States Patent
Tajima

(10) Patent No.: US 11,204,358 B2
(45) Date of Patent: Dec. 21, 2021

(54) SPECIMEN PROCESSING AND MEASURING SYSTEM

(71) Applicant: UNIVERSAL BIO RESEARCH CO., LTD., Chiba (JP)

(72) Inventor: Hideji Tajima, Chiba (JP)

(73) Assignee: UNIVERSAL BIO RESEARCH CO., LTD., Chiba (JP)

( * ) Notice: Subject to any disclaimer, the term of this patent is extended or adjusted under 35 U.S.C. 154(b) by 271 days.

(21) Appl. No.: 16/303,121

(22) PCT Filed: May 25, 2017

(86) PCT No.: PCT/JP2017/019453
§ 371 (c)(1),
(2) Date: Nov. 19, 2018

(87) PCT Pub. No.: WO2017/204274
PCT Pub. Date: Nov. 30, 2017

(65) Prior Publication Data
US 2020/0209268 A1    Jul. 2, 2020

(30) Foreign Application Priority Data

May 25, 2016 (JP) .............................. JP2016-104287
Jan. 20, 2017 (JP) .............................. JP2017-008415

(51) Int. Cl.
*G01N 35/02* (2006.01)
*C12N 15/10* (2006.01)
(Continued)

(52) U.S. Cl.
CPC ....... *G01N 35/025* (2013.01); *C12N 15/1003* (2013.01); *C12Q 1/6844* (2013.01);
(Continued)

(58) Field of Classification Search
CPC .......... B01L 2300/021; B01L 3/50851; B01L 3/545; C12M 1/00; C12N 15/1003;
(Continued)

(56) References Cited

U.S. PATENT DOCUMENTS 5,305,650 A   4/1994 Koike et al.
6,413,780 B1   7/2002 Bach et al.
(Continued)

FOREIGN PATENT DOCUMENTS

CN      101838609 A     9/2010
CN      102066950 A     5/2011
(Continued)

OTHER PUBLICATIONS

English translation of Tajima et al (WO 2014/014016) (Year: 2014).*

(Continued)

*Primary Examiner* — Jennifer Wecker
*Assistant Examiner* — Jonathan Bortoli
(74) *Attorney, Agent, or Firm* — Troutman Pepper Hamilton Sanders LLP

(57) ABSTRACT

A specimen treating and measuring system according to the present invention comprises: a treatment part having a plurality of lanes for carrying out parallel processing of a plurality of specimens, and mounting cartridges in each of the plurality of lanes; a cartridge storing unit storing a plurality of types of cartridge to be used for different processes corresponding to the plurality of specimens; a sample storing unit storing and conveying sample tubes containing the plurality of specimens; a pickup unit transferring each of the plurality of types of cartridge to each lane, and transferring each of the plurality of specimens from the sample tubes to each of the plurality of lanes; and a control unit controlling the transfer of the plurality of types (Continued)

of cartridge and the transfer of the plurality of specimens, performed by the pickup unit.

22 Claims, 26 Drawing Sheets

(51) Int. Cl.
  *C12Q 1/6844* (2018.01)
  *G01N 35/00* (2006.01)
  *G01N 35/10* (2006.01)
(52) U.S. Cl.
  CPC ..... *G01N 35/00732* (2013.01); *G01N 35/026* (2013.01); *G01N 35/1002* (2013.01); *G01N 2035/00346* (2013.01)
(58) Field of Classification Search
  CPC ........ C12C 1/6844; G01N 2035/00346; G01N 2035/00435; G01N 2035/0415; G01N 2035/0436; G01N 35/00732; G01N 35/0095; G01N 35/02; G01N 35/025; G01N 35/026; G01N 35/1002; G01N 35/1011; G01N 2035/0465; C12Q 1/6844
  See application file for complete search history.

(56) References Cited

U.S. PATENT DOCUMENTS

| | | |
|---|---|---|
| 6,509,193 B1 | 1/2003 | Tajima |
| 7,241,304 B2 | 7/2007 | Boyle et al. |
| 8,285,668 B2 | 10/2012 | Kaiser |
| 10,617,435 B2 | 4/2020 | Vale et al. |
| 2002/0127727 A1 | 9/2002 | Bach et al. |
| 2004/0134750 A1 | 7/2004 | Luoma, II |
| 2007/0233175 A1 | 10/2007 | Zaver et al. |
| 2011/0104703 A1 | 5/2011 | Maeda et al. |
| 2011/0262919 A1 | 10/2011 | Tajima |
| 2012/0058900 A1 | 3/2012 | Gisler et al. |
| 2012/0301903 A1 | 11/2012 | Putnam et al. |
| 2013/0130369 A1 | 5/2013 | Wilson et al. |
| 2013/0144311 A1 | 6/2013 | Fung et al. |
| 2014/0087370 A1 | 3/2014 | Maeshima |
| 2015/0032144 A1 | 1/2015 | Holloway |
| 2015/0150672 A1 | 6/2015 | Ma |
| 2015/0202624 A9 | 7/2015 | Putnam et al. |
| 2015/0218618 A1 | 8/2015 | Tajima et al. |
| 2015/0273469 A1* | 10/2015 | Reed .................. B01L 3/50853 141/1 |
| 2016/0025722 A1 | 1/2016 | Tajima |
| 2016/0158750 A1 | 6/2016 | Putnam et al. |
| 2017/0119409 A1 | 5/2017 | Ma |

FOREIGN PATENT DOCUMENTS

| | | | |
|---|---|---|---|
| CN | 102246043 A | 11/2011 | |
| CN | 102455303 A | 5/2012 | |
| CN | 103562727 A | 2/2014 | |
| CN | 103649759 A | 3/2014 | |
| JP | 04-164257 A | 6/1992 | |
| JP | 2003-522322 A | 7/2003 | |
| JP | 3682302 B2 | 5/2005 | |
| JP | 2007-524842 A | 8/2007 | |
| JP | 2013-535193 A | 8/2007 | |
| JP | 2011-185930 | 9/2011 | |
| JP | 2011-220857 A | 11/2011 | |
| JP | 2019-526365 A | 9/2019 | |
| WO | 2010/074265 A1 | 7/2010 | |
| WO | WO-2012012779 A2 * | 1/2012 | ............. C12Q 1/686 |
| WO | 2014-014016 A1 | 1/2014 | |

OTHER PUBLICATIONS

International Search Report dated Aug. 15, 2017 during the prosecution of International Patent Application No. PCT/JP2017/019453.
Notice of Reasons for Refusal issued in corresponding Japanese Patent Application No. 2018-519592 dated Nov. 17, 2020, with machine translation.
Notification of Reasons for Refusal issued in corresponding Japanese Design Patent Application No. 2020-027634 dated Jun. 1, 2021, English translation only.

* cited by examiner

SPECIMEN PROCESSING AND MEASURING SYSTEM

CROSS-REFERENCE TO RELATED APPLICATIONS

This is a U.S. national phase application under 35 U.S.C. § 371 of International Patent Application No. PCT/JP2017/019453, filed May 25, 2017, and claims benefit of priority to Japanese Patent Application Nos. 2016-104287 and 2017-008415, filed May 25, 2016 and Jan. 20, 2017 respectively. The entire contents of these applications are hereby incorporated by reference.

TECHNICAL FIELD

The present invention relates to a specimen treatment and measurement system for continuously executing treatment and measurement on samples (specimens) of a plurality of types of biologically relevant materials.

BACKGROUND

A sample of a biologically relevant material such as a gene is subjected to predetermined pretreatment and then subjected to measurement processing such as detection or quantification. As the predetermined pretreatment, the sample is subjected to physical treatment, such as capturing, refinement, separation and/or cleaning, gene amplification, chemical treatment, and/or some other treatment. As the measurement processing, chemiluminescence, luminescence, adsorbance, and the like are measured. For performing such pretreatment and measurement, it is necessary to select plastic members and consumables such as dispensation chips for dispensing a plurality of reagents, reaction solutions, and the like in accordance with a treatment purpose, and to execute an appropriate pretreatment step by sequentially using these.

The present inventor has proposed magtration technology in U.S. Pat. No. 3,682,302, FIG. 3 using magnetic particles. In addition to the magtration technology, the present inventor has made it possible to perform polyspecimen batch treatment by cartridge multiple row alignment, simultaneous control of solution dispensation with a plurality of dispensation nozzles, and dispensation control using separation of a magnetic body, as proposed in WO2010/074265, FIG. 38.

As automatization of the pretreatment, two systems have been proposed, which are a multi-sample batch system and a one-sample random access system. The multi-sample batch system is to perform batch treatment on a plurality of samples in parallel. Examples of a multi-sample batch system product include "geneLEAD XII" supplied by Precision System Science Co., Ltd. Examples of a multi-sample batch system product include "cobas" series supplied by Roche Diagnostics K.K. The one-sample random access system is to read information piece by piece for each sample and sequentially execute different physical treatment and reaction treatment based on the information.

SUMMARY

The advantage of the multi-sample batch system is being able to downsize and simplify the device by performing batch treatment on a plurality of samples in a "system configuration where each functioning part for treatment is stabilized". However, the disadvantage of the multi-sample batch system is having difficulties in dealing with samples required to be subjected to a plurality of different steps and dealing with continuously introduced different samples. Specifically, as shown in FIG. 1, a case is assumed where a plurality of samples $S_{A1}$, $S_{A2}$, $S_{A3}$, $S_{A4}$, $S_{A5}$, $S_{A6}$, $S_{AB1}$, and $S_{BC1}$ are treated in the multi-sample batch system. The samples $S_{A1}$, $S_{A2}$, $S_{A3}$, $S_{A4}$, $S_{A5}$, and $S_{A6}$ need to be subjected to pretreatment of an item A while not needing to be subjected to pretreatment of an item B or an item C. The sample $S_{AB1}$ needs to be subjected to the pretreatment of the item A and the pretreatment of the item B while not needing to be subjected to the pretreatment of the item C. The sample $S_{BC1}$ needs to be subjected to the pretreatment of the item B and the pretreatment of the item C sequentially while not needing be subjected to the pretreatment of the item A. As thus described, it is difficult to simultaneously perform the multiple-sample batch treatment on a plurality of samples for which necessary items are different.

In contrast, the advantage of the one-sample random access system is being able to perform treatment on samples, required to be subjected to a plurality of steps of treatment (items), in a consistent and continuous manner. However, as shown in FIG. 2, the disadvantage of the one-sample random access system is needing to transfer the sample from a specified functioning part to another specified functioning part for treatment and to respectively execute different treatment steps. Due to the treatment step being different for each sample, hardware and software for controlling the treatment steps become complex. As a result, a problem has occurred where a required system or device becomes extremely complex, high in price, and large in size (5 m to 10 m). For example, as shown in FIG. 2, a case is assumed where the samples $S_{A1}$, $S_{AB1}$, $S_{BC1}$ are treated in the one-sample random access system. First, the sample $S_{A1}$ is transferred to an item-A treatment functioning part and subjected to the treatment step of the item A, whereafter the sample $S_{A1}$ is transferred to a sample collector. Next, the sample $S_{AB1}$ is transferred to the item-A treatment functioning part and subjected to the treatment step of the item A, and the sample $S_{AB1}$ is transferred to an item-B treatment functioning part and subjected to the treatment step of the item B, whereafter the sample $S_{AB1}$ is transferred to the sample collector. Finally, the sample $S_{BC1}$ is transferred to the item-B treatment functioning part and subjected to the treatment step of the item B, and the sample $S_{BC1}$ is transferred to the item-C treatment functioning part and subjected to the treatment step of the item C, whereafter the sample $S_{BC1}$ is transferred the sample collector. Further, since the treatment is performed for each sample in the one-sample random access system, there has occurred a problem where a great deal of time is required in the case of performing treatment on a plurality of samples.

Requirements in an automated system of the pretreatment step on the plurality of samples are as follows: There are as many as tens of types of required test items, thereby requiring an information management system which accurately makes selection using a bar code or an IC tag without selecting a wrong reagent or consumable. Further, it is necessary to consider a contamination preventive measure for preventing mixture of even a trace of reagent and sample, and a stage layout and a transfer method for achieving storage, supply, and disposal of a large amount of reagent and consumable, so as to continuously perform treatment on as large an amount of sample as possible. In addition, it is necessary to consider a structure capable of ensuring continuous treatment on a large number of samples, an interruption function of a priority specimen for an urgent test, user friendly interface easy to use by an operator, and downsizing, a low price, and reliable safety of a device body.

It is an object of the present invention to provide a new specimen treatment and measurement system that is capable of efficiently and continuously executing treatment and measurement when treatment is performed on a plurality of specimens.

Each aspect of the present invention is as follows:

(Aspect 1) A specimen treatment and measurement system for executing treatment in parallel which is made up of extraction of nucleic acid contained in each of a plurality of specimens, amplification of the extracted nucleic acid, and measurement of the amplified nucleic acid, the system including: a cartridge storing unit that stores one type or a plurality of types of cartridges for use in the treatment corresponding to the plurality of specimens; a specimen treatment part including a plurality of treatment lanes configured to execute the treatment in parallel, the cartridge being installed on each of the plurality of treatment lanes; a specimen storing unit that stores each of the plurality of specimens; a cartridge transferring unit that transfers the plurality of cartridges to the plurality of lanes, respectively; a specimen transferring unit that transfers the plurality of specimens to the plurality of treatment lanes; and a controller that controls the transfer of the cartridge by the cartridge transferring unit and the transfer of the plurality of specimens by the specimen transferring unit, and in the system, the controller uses the cartridge transferring unit to transfer to each of the plurality of treatment lanes the cartridge corresponding to each of the plurality of specimens, and the controller further uses the specimen transferring unit to transfer the plurality of specimens to the plurality of treatment lanes.

(Aspect 2) The specimen treatment and measurement system according to the aspect 1, where the treatment and/or the measurement is batch treatment that is simultaneously performed on the plurality of specimens. (Aspect 3) The specimen treatment and measurement system according to the aspect 1 or 2, including a specimen treatment preparing unit obtained by integrating the cartridge transferring unit and the specimen transferring unit.

(Aspect 4) The specimen treatment and measurement system according to any one of the aspects 1 to 3, where at least a part of the cartridge includes a prefilled well in which a reagent and/or a solution required for the treatment is sealed in advance. (Aspect 5) The specimen treatment and measurement system according to any one of the aspects 1 to 4, where the plurality of specimens are classified into a plurality of groups among which common treatment operation is possible, and the controller selects a plurality of specimens, included in the same group, from the plurality of specimens and executes the treatment in parallel.

(Aspect 6) The specimen treatment and measurement system according to the aspect 5, where the treatment is executed in parallel on the plurality of specimens for each group altogether to perform treatment on a whole of the plurality of specimens in a random and continuous manner.

(Aspect 7) The specimen treatment and measurement system according to any one of the aspects 1 to 6, where the cartridge transferring mechanism includes a cartridge picker that adsorbs the at least one cartridge. (Aspect 8) The specimen treatment and measurement system according to the aspect 7, where the cartridge picker vacuum-sucks the cartridge.

(Aspect 9) The specimen treatment and measurement system according to the aspect 7 or 8, where the cartridge picker includes a protrusion, and the cartridge includes a recess into which the protrusion is inserted. (Aspect 10) The specimen treatment and measurement system according to any one of the aspects 7 to 9, where the cartridge picker adsorbs both ends of the cartridge. (Aspect 11) The specimen treatment and measurement system according to any one of the aspects 7 to 10, where the cartridge transferring mechanism includes a cartridge-picker lifting mechanism that lifts and lowers the cartridge picker. (Aspect 12) The specimen treatment and measurement system according to any one of the aspects 7 to 11 where the specimen treatment and measurement system includes a consumable storing unit that stores a consumable for use in the plurality of lanes, and the cartridge transferring mechanism includes a consumable picker that takes the consumable out of the consumable storing unit.

(Aspect 13) The specimen treatment and measurement system according to the aspect 12, where the cartridge transferring mechanism includes a consumable-picker lifting mechanism that lifts and lowers the consumable picker. (Aspect 14) The specimen treatment and measurement system according to any one of the aspects 7 to 13, where the cartridge includes a cartridge information recording part in which cartridge information is recorded, and the cartridge transferring mechanism includes an information reading part that reads the cartridge information out of the cartridge information memory. (Aspect 15) The specimen treatment and measurement system according to any one of the aspects 1 to 14, where a first cartridge and a second cartridge are installed on each of the plurality of treatment lanes, and the controller removes the second cartridge with the treatment on the specimen terminated from the plurality of treatment lanes by using the cartridge transferring mechanism, while treatment is performed on the specimen in the first cartridge. (Aspect 16) The specimen treatment and measurement system according to any one of the aspects 1 to 15, where the specimen container includes a specimen information recording part in which specimen information and/or reagent information for use in treatment on the specimen is recorded, and the specimen transferring unit or the specimen storing unit includes an information reading part that reads the specimen information and/or the reagent information out of the specimen information memory.

(Aspect 17) The specimen treatment and measurement system according to any one of the aspects 1 to 16, where the specimen storing unit includes a specimen conveying mechanism that circularly conveys the plurality of specimens, and a specimen takeout position for taking the specimen out of the specimen conveying mechanism. (Aspect 18) The specimen treatment and measurement system according to any one of the aspects 1 to 17, where the specimen storing unit includes a temperature adjusting mechanism for preventing degeneration or deterioration of the plurality of specimens. (Aspect 19) The specimen treatment and measurement system according to any one of the aspects 1 to 18, including a cartridge fixing mechanism that fixes the cartridge to the specimen treatment part. (Aspect 20) The specimen treatment and measurement system according to any one of the aspects 1 to 19, where the cartridge fixing mechanism includes a first claw and a second claw that push both ends of the cartridge. (Aspect 21) The specimen treatment and measurement system according to any one of the aspects 1 to 20, including a treatment executing unit that has a plurality of dispensation nozzles so as to execute the treatment in parallel on the cartridge installed in each of the plurality of treatment lanes. (Aspect 22) The specimen treatment and measurement system according to any one of the aspects 1 to 21, including a measurement unit for executing the measurement of the plurality of specimens.

(Aspect 23) A specimen treatment and measurement system for executing treatment in parallel which is made up of extraction of nucleic acid contained in each of a plurality of specimens, amplification of the extracted nucleic acid, and measurement of the amplified nucleic acid, and in the system, the specimen treatment and measurement system includes a treatment preparation sub-system, a treatment execution sub-system, a plurality of stage racks, a stage-rack transferring mechanism that transfers the plurality of stage racks between the treatment preparation sub-system and the treatment execution sub-system, and a controller that controls operation of the specimen treatment and measurement system, the treatment preparation sub-system includes a cartridge supply unit that supplies at least one cartridge, a cartridge picker that picks up the cartridge, a consumable storing unit which stores a consumable, a pickup unit that picks up the consumable, and a specimen storing part that stores the plurality of specimens, each of the plurality of stage racks includes a plurality of treatment lanes so as to execute the treatment in parallel, and the cartridge, the consumable, and the specimen container are installed in predetermined positions in each of the plurality of treatment lanes, and the treatment execution sub-system includes a plurality of treatment executing units, a plurality of stage-rack mounting parts in which the plurality of stage racks are mounted, and a stage-rack mounting mechanism that transfers each of the stage racks to the stage-rack mounting part, and each of the plurality of treatment executing units executes the treatment on each of the plurality of specimens on the stage rack mounted in the stage-rack mounting part.

(Aspect 24) The specimen treatment and measurement system according to the aspect 23, where a plurality of specimens, to which a common protocol capable of executing the treatment in parallel is applied, are arranged in one stage rack, and the treatment is executed in one treatment executing unit. (Aspect 25) The specimen treatment and measurement system according to the aspect 23 or 24, where in each of the plurality of treatment lanes, an extraction functioning part that extracts nucleic acid from the specimen, an amplification functioning part that amplifies the extracted nucleic acid, and the measurement functioning part that measures the amplified nucleic acid are arranged in a line. (Aspect 26) The specimen treatment and measurement system according to any one of the aspects 23 to 25, where the stage rack installs, on each of the treatment lanes, a reagent container accommodating various reagents for use in the treatment, the cartridge, the consumable, and a specimen container that contains the specimen, and all or at least some of these are replaced or disposed of after the treatment to enable reduction in contamination of the specimen.

(Aspect 25) The specimen treatment and measurement system according to the aspect 23 or 24, where the cartridge picker vacuum-sucks the cartridge. (Aspect 26) The specimen treatment and measurement system according to any one of the aspects 23 to 25, where the cartridge picker adsorbs both ends of the cartridge. (Aspect 27) The specimen treatment and measurement system according to any one of the aspects 23 to 26, including a transport mechanism that transports a reagent and/or a specimen for use in the treatment from the treatment preparation sub-system to the treatment execution sub-system when the reagent and/or the specimen is used in the treatment executing unit.

(Aspect 28) The specimen treatment and measurement system according the aspect 27, where the transport mechanism is made up of a slide rack that accommodates the reagent or the specimen, and a slide mechanism that slides the slide rack. (Aspect 29) The specimen treatment and measurement system according to the aspect 26 or 27, where the treatment preparation sub-system further includes a storage part that adjusts a temperature of the reagent or the specimen and stores the reagent or the specimen. (Aspect 30) The specimen treatment and measurement system according to any one of the aspects 23 to 29, where the cartridge supplying unit includes a cartridge push-out mechanism that pushes a bottom cartridge of a stacked plurality of cartridges out of the cartridge supplying unit. (Aspect 31) The specimen treatment and measurement system according to any one of the aspects 23 to 30, where the treatment execution sub-system further includes an adhesion mechanism that causes a heat block to adhere to the stage rack mounted in the stage-rack mounting part. (Aspect 32) The specimen treatment and measurement system according to any one of the aspects 23 to 31, where the treatment execution sub-system includes a consumable tank that disposes of the consumable, and the dispensation nozzle of the treatment executing unit takes out the consumable from the stage rack and disposes of the consumable into the consumable tank during the treatment or after the treatment.

(Aspect 33) The specimen treatment and measurement system according to the aspects 23 to 32, where the treatment execution sub-system includes a waste liquid tank that disposes of a waste liquid containing the specimen, and the dispensation nozzle of the treatment executing unit sucks the waste liquid from the stage rack and disposes of the waste liquid into the waste liquid tank during the treatment or after the treatment. (Aspect 34) The specimen treatment and measurement system according to the aspects 23 to 33, where the treatment preparation sub-system includes a cartridge waste part that disposes of the cartridge, and after completion of measurement, the cartridge picker picks up the cartridge from the stage rack transferred to the treatment preparation sub-system and disposes of the cartridge into the cartridge waste part. (Aspect 35) The specimen treatment and measurement system according to any one of the aspects 1 to 34, where the consumable includes at least one of a well, a tube, a dispensation chip, a piercing chip, and a cap of the well. (Aspect 36) The specimen treatment and measurement system according to any one of the aspects 1 to 35, where at least a part of the cartridge includes at least one prefilled well in which an extracted reagent of the nucleic acid and/or an amplified reagent of the nucleic acid is sealed in advance.

(Aspect 37) The specimen treatment and measurement system according to any one of the aspects 1 to 35, where at least a part of the cartridge includes a prefilled cartridge for an extracted reagent in which the extracted reagent of the nucleic acid is sealed in advance, and a prefilled cartridge for an amplified reagent in which an amplified reagent of the nucleic acid is sealed in advance. (Aspect 38) The specimen treatment and measurement system according to any one of the aspects 1 to 35, where the cartridge includes at least one or a plurality of a well for a reagent, a well for extracting nucleic acid, a well for amplifying nucleic acid, a cap holding part that holds a cap of the well, and a dispensation chip holding part that holds a dispensation chip. (Aspect 39) The specimen treatment and measurement system according to any one of the aspects 1 to 38, where the treatment lane includes a tube that accommodates a micro particle for detecting nucleic acid, a plurality of the micro particles, to each of which a material capable of being specifically coupled to a different specimen is fixed, are arranged at known positions in the tube, and the specimen treatment and measurement system is provided with a detector that detects a signal issued by the micro particle in the tube. (Aspect 40) The specimen treatment and measurement system according to any one of the aspects 1 to 39, where the treatment lane includes an electrophoresis chip that performs electrophoresis of the specimen, and the specimen treatment and measurement system includes a detector that detects a band separated from the specimen in the electrophoresis chip. (Aspect 41) The specimen treatment and measurement system according to any one of the aspects 1 to 40, including a biochemical testing device that conducts a biochemical test of the specimens.

In the specimen treatment and measurement system of the present invention, it is possible to efficiently execute continuous treatment in the case of performing treatment on a plurality of specimens that requires different treatment steps.

DETAILED DESCRIPTION

Figure 1:
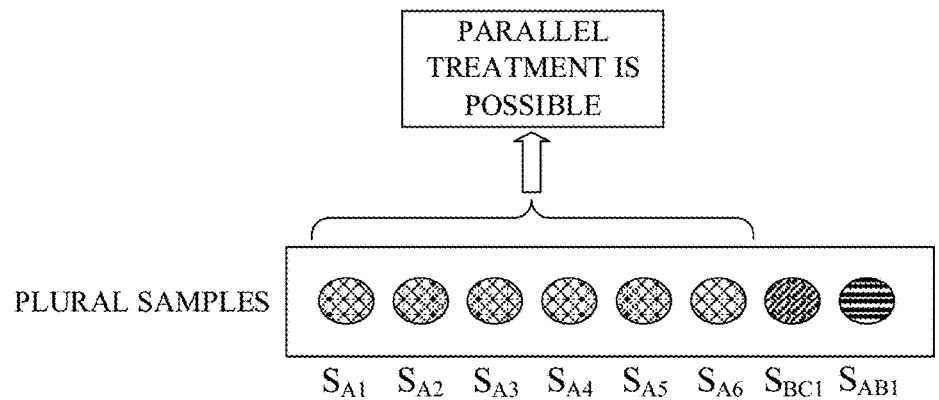
FIG. 1 is a schematic diagram for explaining a multi-sample batch system.
Figure 2:
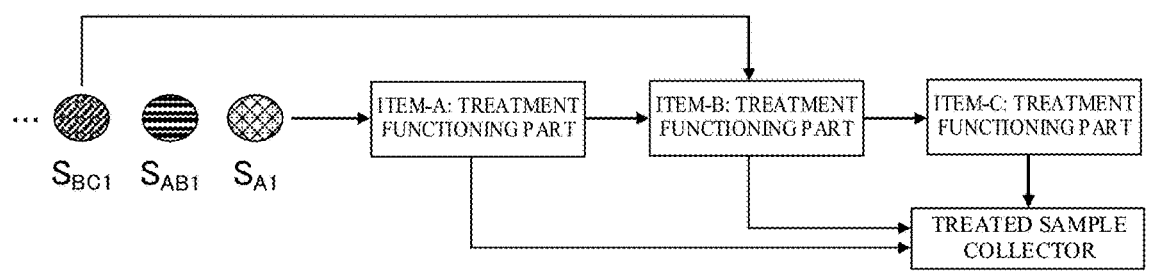
FIG. 2 is a schematic diagram for explaining a one-sample random access system.
Figure 3:
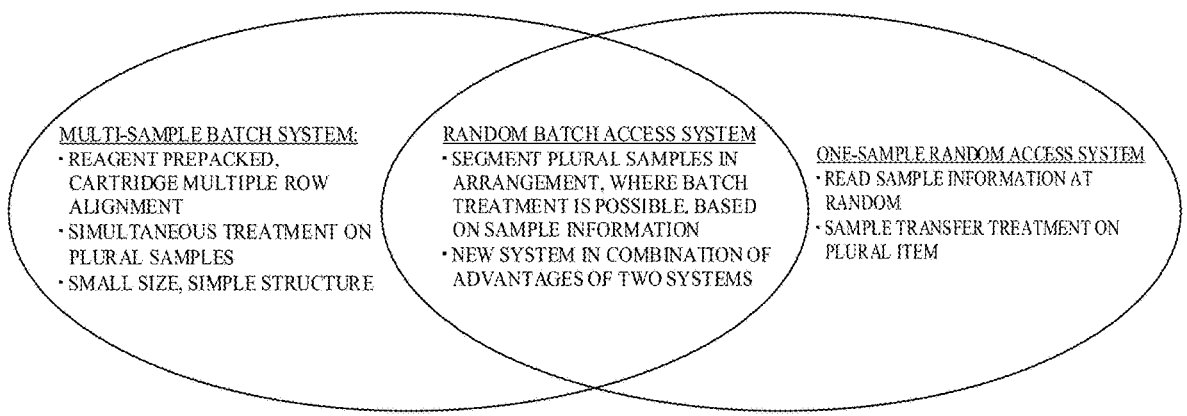
FIG. 3 is a venn diagram concerning a random batch access system of the present invention.

A specimen treatment and measurement system according to each embodiment of the present invention will be described with reference to the drawings. The description will be given as the same numeral is given to the same portion in the drawings. As shown in FIG. 3, each embodiment of the present invention provides a specimen treatment and measurement system of a random batch access system obtained by combining the conventional multi-sample batch system and one-sample random access system. In each embodiment of the present invention, "treatment" includes extraction, refinement, and amplification of a specimen containing nucleic acid, and "measurement" includes measurement of a pretreated specimen (nucleic acid), such as measurement of a band by real time polymerase chain reaction (PCR) or gel electrophoresis. In the case of the real time PCR, the amplification and the measurement are performed simultaneously.

First Embodiment

<Summary of Specimen Treatment and Measurement System>

Figure 4:
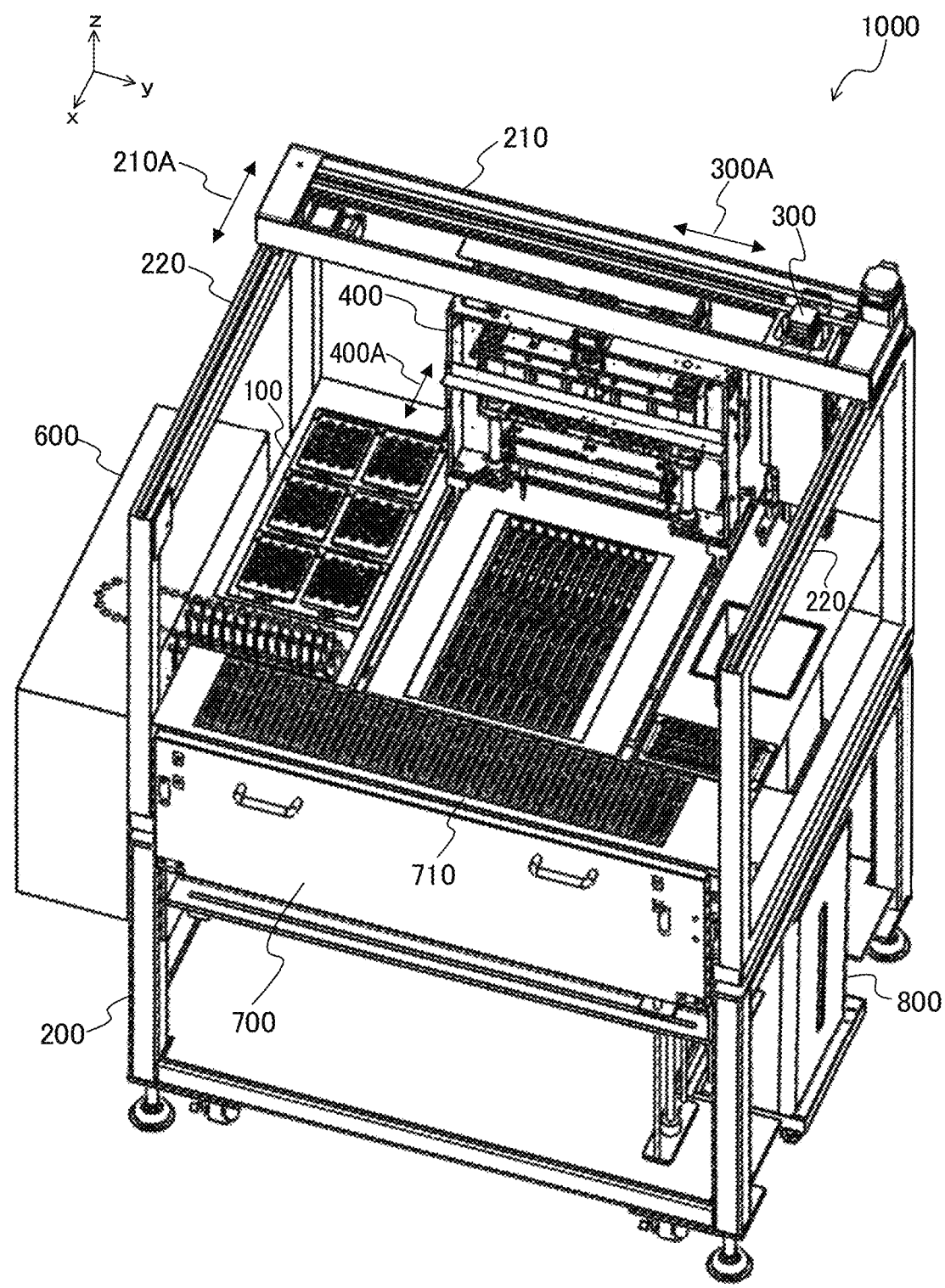
FIG. 4 is a perspective view of a specimen treatment and measurement system according to a first embodiment of the present invention.

A summary of a sample treatment and measurement system 1000 according to a first embodiment will be described with reference to FIG. 4. The specimen treatment and measurement system 1000 includes: a stage 100 that executes each treatment step while holding a consumable and the like; a frame 200 to which the stage 100, each unit, and the like are attached; a pickup unit (picker unit) 300 that is movably attached to the frame 200 in an x-direction 210A and a y-direction 300A; a treatment executing unit 400 movably provided in an x-direction 400A on the stage 100;

a sample storing unit 600; a cartridge storing unit 700 that stores a plurality of types of cartridges for use in treatment; a waste box 800 provided below the stage 100; and a controller, not shown, for controlling operation of each unit. The treatment etc. executing unit 400 includes a plurality of dispensation nozzles (nozzle part) that correspond to a plurality of treatment lanes and move up and down in a unified manner.

<Stage>

Figure 5:
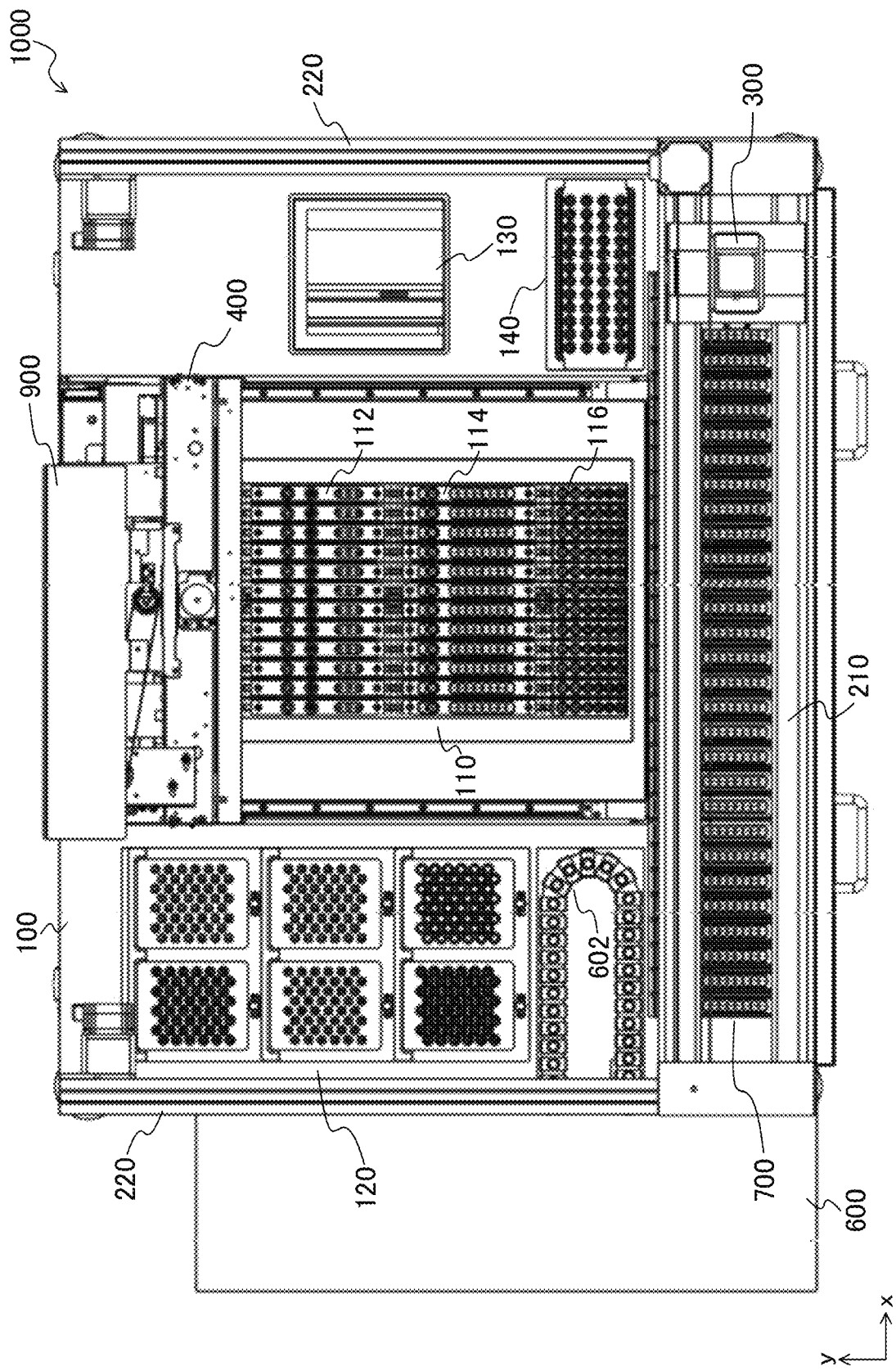
FIG. 5 is a top view of the specimen treatment and measurement system of FIG. 4.

The stage 100 of the specimen treatment and measurement system 1000 will be described with reference to the top view of FIG. 5. The following are provided on the stage 100: a treatment part 110 including a plurality of treatment lanes; a consumable storing unit 120 that stores a consumable such as a dispensing chip, a sample tube, or a cap; a consumable waste port 130 connected to the waste box 800; and an extract etc. storing rack 140 that stores an extract, its residual liquid, and the like. Further, the sample storing unit 600 is placed lateral to the stage 100, and the sample storing unit 600 includes a sample-tube conveying chain conveyer 602 that conveys a plurality of sample tubes. A part of the chain conveyer 602 is extended from the sample storing unit 600 to the stage 100 side. A measurement unit 900 for measuring the amplified sample is provided behind the treatment etc. executing unit 400.

Each treatment lane of the treatment part 110 is made up of a cartridge (first treatment cartridge) 112 for extracting nucleic acid, a cartridge (second treatment cartridge) 114 for amplifying and measuring nucleic acid, and a consumable accommodating part 116 that accommodates a consumable such as a dispensation chip or a cap for use in each treatment step. On each treatment lane, the cartridges 112, 114, and the consumable accommodating part 116 are arranged linearly. Each treatment lane of the treatment part 110 can include at least one cartridge. While moving along the treatment lane above the treatment part 110, the treatment etc. executing unit 400 sucks and discharges a reagent or a solution from and into a sample in the well of the cartridge to execute treatment by using a dispensation (dispensation nozzle) of the movement unit 400. The cartridges 112, 114 preferably include a linearly arranged plurality of wells (containers). The wells and the cartridges may not be integrated, but at least one well may be placed in the treatment part 110 together with the cartridges 112, 114.

<Chain Conveyer (Sample Conveying Mechanism)>

Figure 6:
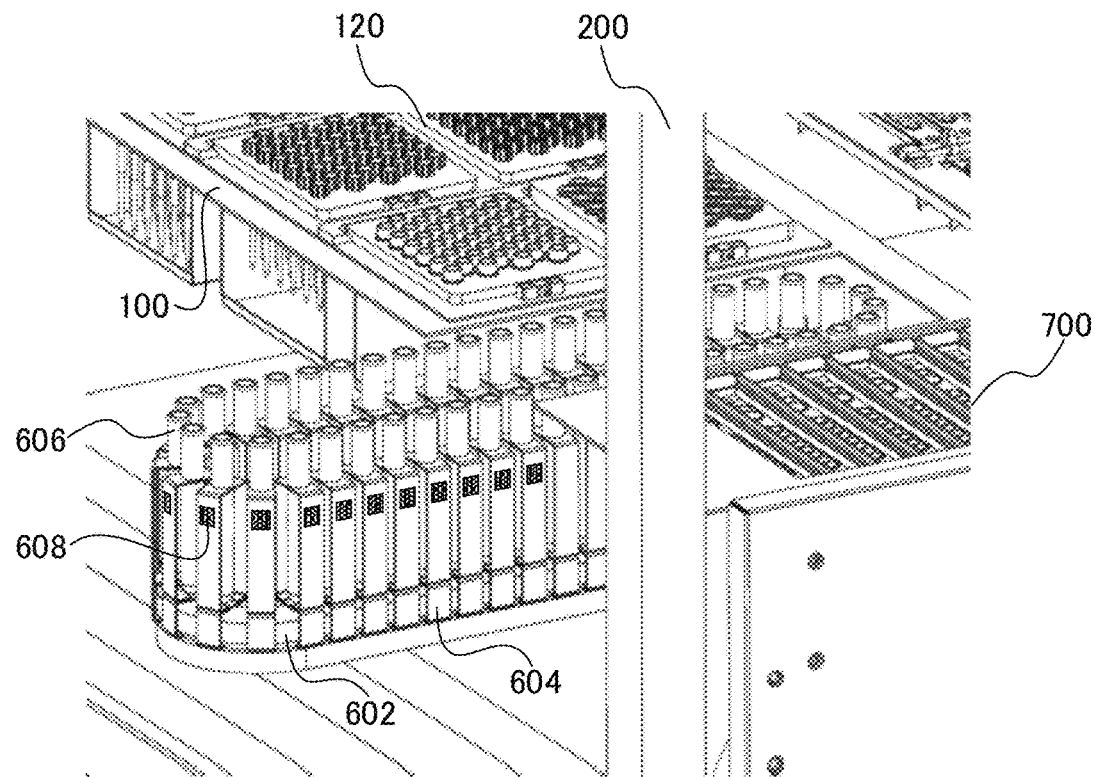
FIG. 6 is a perspective view of a chain conveyer in the specimen treatment and measurement system of FIG. 5.
Figure 7:
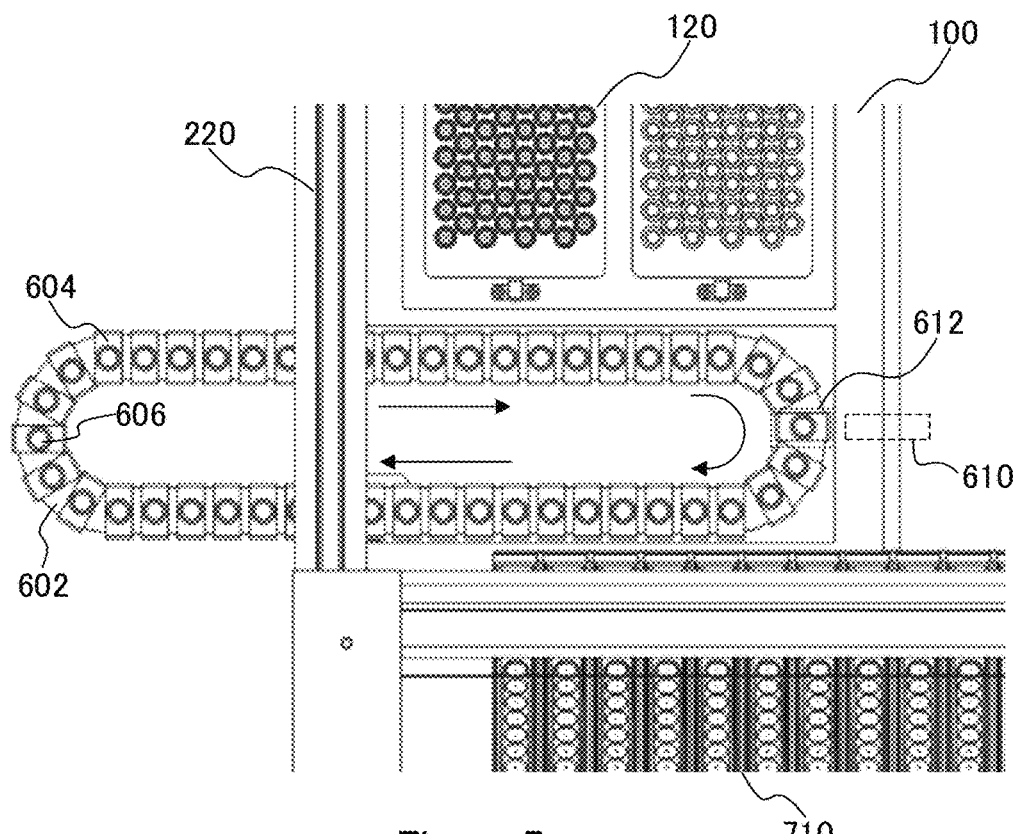
FIG. 7 is a top view of the chain conveyer of FIG. 6.

The chain conveyer 602 of the sample storing unit 600 will be described with reference to a perspective view of FIG. 6 and a top view of FIG. 7. In FIGS. 6 and 7, a housing of the sample storing unit 600 and a drive mechanism of the chain conveyer 602 are not shown. On the chain conveyer 602, a plurality of tube holders (main specimen trays) 604 are arranged, and a sample tube (main specimen container) 606 accommodating a sample is held in the tube holder 604. An information memory 608 that stores sample information and/or information concerning a reagent to be used may preferably be included on the surface of the tube holder 604 or the sample tube 606 which faces outward or upward. The information memory 608 can be a QR code (registered trademark), a bar code, an IC tag, or the like. An information reading part 610 is provided at a position facing the information memory 608. Note that information of the information memory 608 may be read by an information reading part 350 (FIG. 9) instead of the information reading part 610. The chain conveyer 602 is rotated and driven by a drive mechanism, not shown. Further, the sample storing unit 600 can preferably be provided with a temperature adjustment mechanism for preventing degeneration or deterioration of a sample in the sample tube 606. For example, when the sample is whole blood, the temperature adjustment mechanism keeps the sample tube 606 at 2 to 6° C.

The sample tube 606 moves on an annular orbit of the chain conveyer (sample conveying mechanism) 602. In a state where the sample tube 604 has moved to a takeout position 612 on the stage 100 side, a specimen in the sample tube 606 can be taken out (sucked) by the dispensation nozzle of a preparing movement unit 300. The information reading part 610 can be provided at a position facing the takeout position 612. This makes it possible to read information at the time of taking the sample out of the sample tube 606.

The sample tubes 604 can preferably be arrayed at random on the chain conveyer 602 by opening an upper lid (not shown) of the chain conveyer 602. Even when the sample tubes are arrayed at random, it is possible to continuously take out a plurality of samples, which can be subjected to parallel treatment, by the information reading part 610 or 350 reading information out of the information memory 608 in each sample tube 606. The controller of the specimen treatment and measurement system 1000 of the first embodiment can preferably be provided with a priority sample interruption function for a test of a priority sample needing to be tested urgently. For example, when a priority sample requiring urgent treatment or test is generated, the priority sample interruption function can be executed. For example, at the time of executing the priority sample interruption function, based on the information read by the information reading part 610 or 350, the chain conveyer 602 can be driven to move the sample tube 606 of the priority sample to the takeout position 612 to be taken out prior to the other samples, to execute the treatment.

<Pickup Unit>

Figure 8:
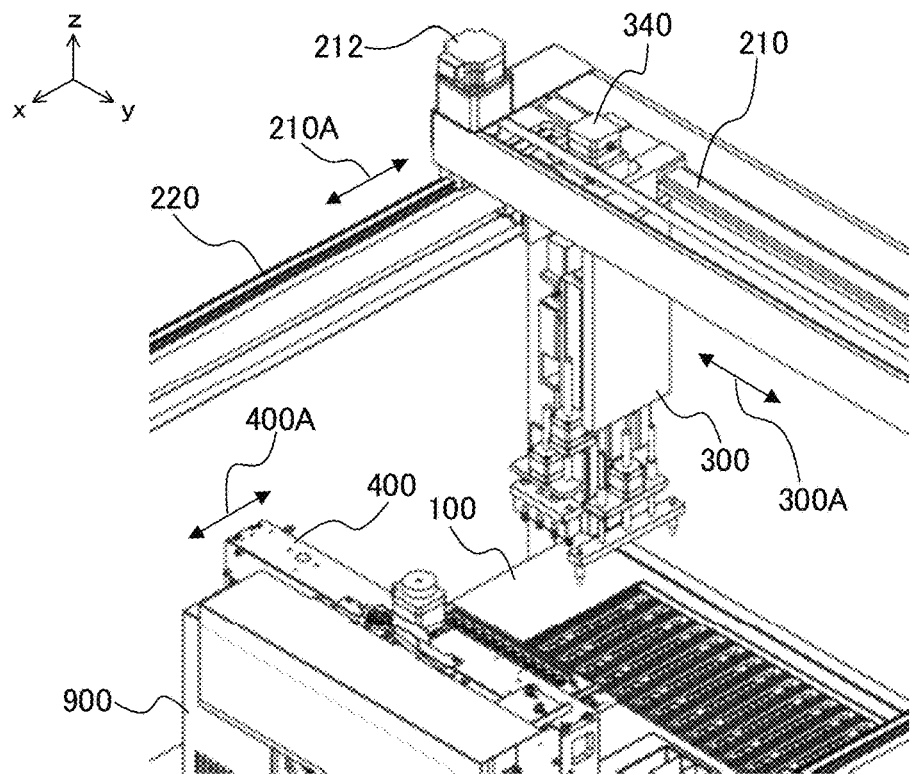
FIG. 8 is a top perspective view of a pickup unit installed in the specimen treatment and measurement system of FIG. 4.
Figure 9:
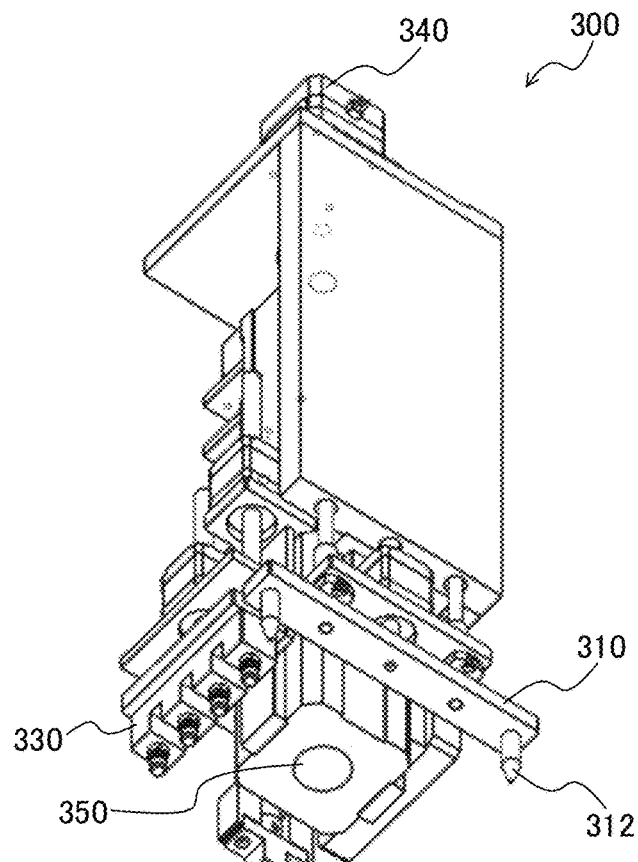
FIG. 9 is a bottom perspective view of the pickup unit of FIG. 8.
Figure 10:
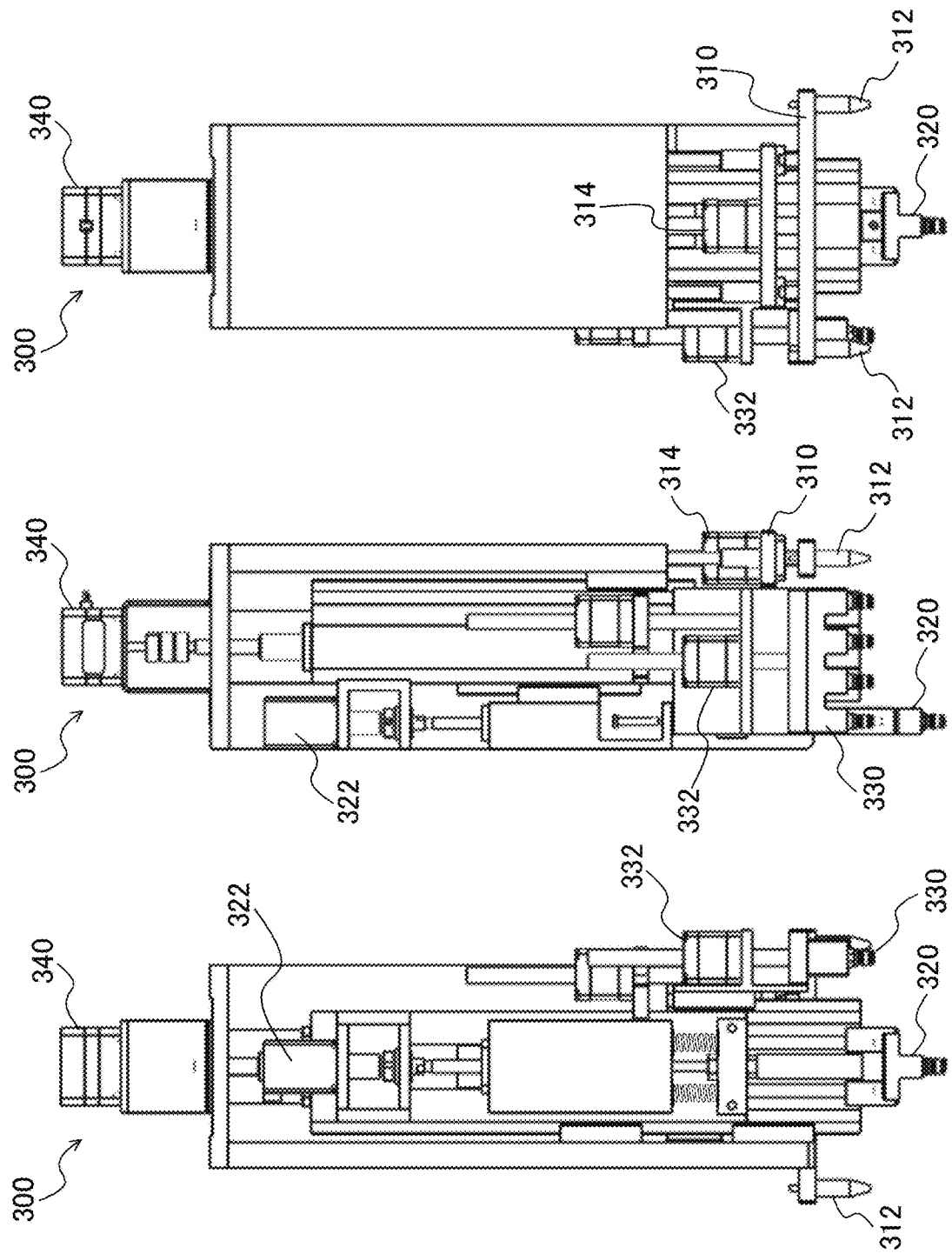
FIGS. 10(a) to 10(c) are side views of the pickup unit of FIG. 8.

A pickup unit 300 will be described with reference to FIGS. 8 to 10. The pickup unit 300 is movably provided above the stage 100 as shown in FIG. 8. The pickup unit 300 is placed on a first rail 210 so as to be movable by a first motor 340 in the y-direction 300A. The first rail 210 is placed on a second rail 220 so as to be movable by a second motor 212 in the x-direction 210A. Note that the second rail 220 is integrated with the frame 200, and as shown in FIG. 4, a pair of second rails 220 are provided at positions corresponding to both ends of the first rail 210.

The pickup unit 300 will be described using a bottom perspective view of FIG. 9. The lower part of the pickup unit 300 is provided with: a cartridge picker (cartridge takeout tool) 310 that conveys the cartridges 112, 114; a nozzle part (dispensation nozzle) 320 to which the dispensing chip is connected; a consumable picker (consumable takeout tool) 330 that takes out a consumable such as the dispensing chip, the tube, or the cap; and the information reading part 350 that reads cartridge information out of information memory of the cartridge, described later.

As shown in FIG. 10(a), the nozzle part 320 can be lifted and lowered by a nozzle-part lifting motor 322 installed in the pickup unit 300. With the dispensation chip in the state of being attached to the nozzle part 320, the nozzle part 320 can suck and discharge a liquid from and to the dispensation chip by using a vacuum pump, not shown. As shown in FIG. 10(b), the consumable picker 330 can be lifted and lowered by the consumable-picker lifting motor 332 installed in the pickup unit 300. Further, the consumable picker 330 includes a plurality of (four in FIG. 10(b)) coupling ends, and by coupling (insertion) of the coupling end into an opening of the dispensing chip, the tube, the cap, or the like, these can be taken out. As shown in FIG. 10(c), the cartridge picker 310 can be lifted and lowered by the cartridge-picker lifting motor 314 installed in the pickup unit 300. Moreover, the cartridge picker 310 includes a pair of adsorption parts (protrusions) 312 that movably adsorbs both ends of the cartridge 112(114). The adsorption part 312 projects in a conical shape and its tip is provided with an opening. The opening of the adsorption part 312 is connected to the vacuum pump, not shown.

Figure 11:
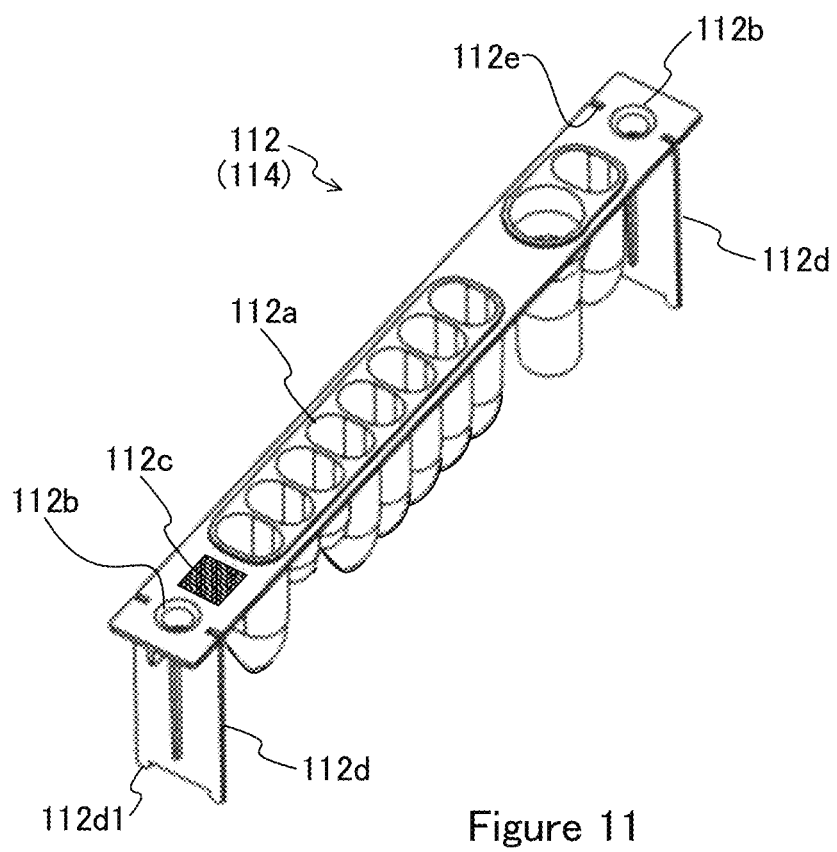
FIG. 11 is a top perspective view of a cartridge according to the first embodiment of the present invention.

A structure of the cartridge 112 will be described with reference to FIG. 11. The cartridge 112 has an elongated shape and includes: a linearly arranged plurality of wells 112a; a pair of adsorbed part (recesses) 112b provided on the top surface at both ends of the cartridge 112; an information recording part 112c provided on the upper surface of the cartridge; a pair of laminating plates 112d extending downward from both ends of the cartridge 112; and a pair of slits 112e provided at both ends of the cartridge 112. Further, a pair of projecting pieces 112d1 are provided at lower ends of the laminating plate 112d. At the time of laminating and storing the cartridges 112, the projecting piece 112d1 of the laminating plate 112d of the upper-side cartridge 112 is detachably engaged into the slit 112e of the lower-side cartridge 112, so that the plurality of cartridges 112 can be laminated in vertical alignment. Although the description has been given of the cartridge 112 in FIG. 11, the cartridge 114 can be structured as is the cartridge 112 except for the placement and shape of the well 112a, namely, the cartridge 114 can be provided with a pair of adsorbed parts, an information memory, a pair of laminating plates, a pair of slits, and a pair of projecting pieces. At least a part of each of the cartridges 112, 114 can be a prefilled cartridge. The prefilled cartridge can be provided with a plurality of prefilled wells in which a reagent or a solution required for the treatment step has been sealed in advance.

Figure 12:
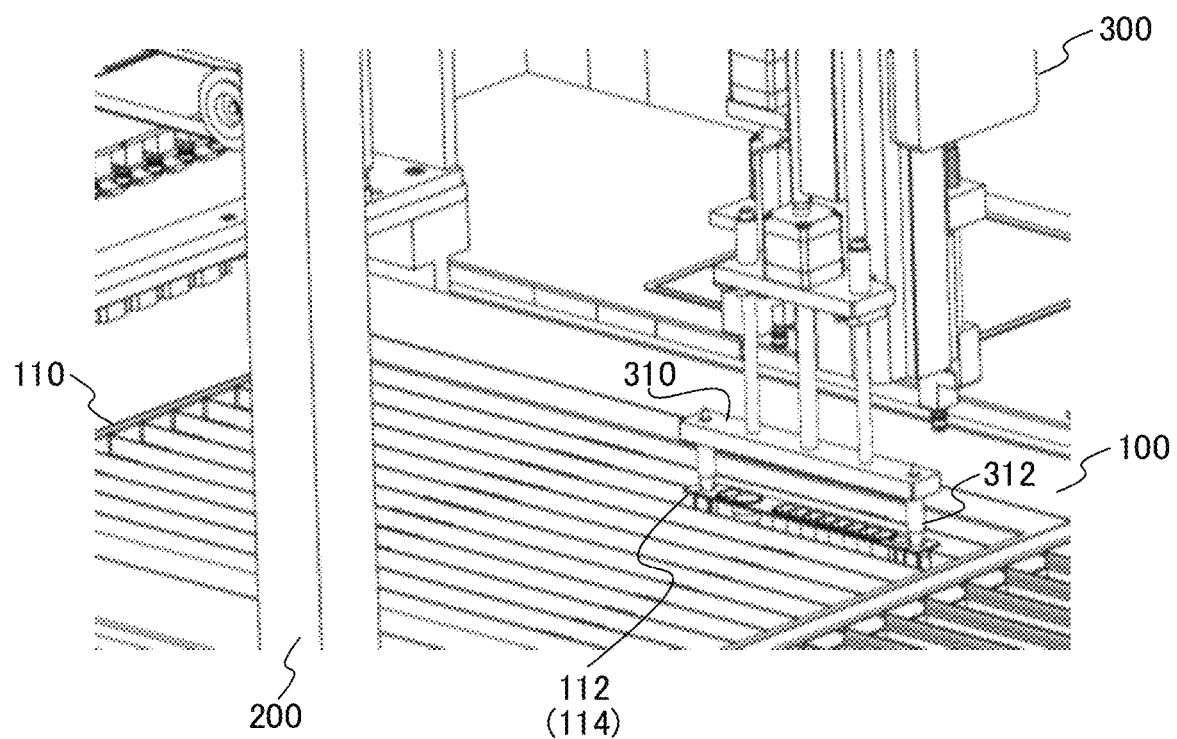
FIG. 12 is a perspective view of a state in which the cartridge of FIG. 11 is set on a stage.

The taking-out and transfer of the cartridge 112 by using the cartridge picker 310 will be described with reference to FIG. 12. The pickup unit 300 moves from the state of FIG. 4, and the pickup unit 300 stops above an outlet 710 on the upper surface of the cartridge storing unit 700. With the pickup unit 300 in the state of being stopped above the outlet 710, the cartridge picker 310 is lowered, and the adsorption part 312 of the cartridge picker 310 is inserted into the adsorbed part 112b of the cartridge 112(114). After the insertion of the adsorption part 312 into the adsorbed part 112b, pressure is reduced from the tip opening of the adsorption part 312 by the vacuum pump, not shown, so that the cartridge 112(114) is adsorbed to the cartridge picker 310. After the cartridge 112(114) in the state of being adsorbed to the adsorption part 312 of the cartridge picker 310 has lifted the cartridge picker 310 to the movement position, the pickup unit 300 is moved to above the treatment part 110. After the movement of the pickup unit 300 to above the treatment part 110, the cartridge picker 310 is lowered, the cartridge 112(114) is placed at a position in a predetermined treatment lane in the treatment part 110, the reduction in pressure of the vacuum pump of the adsorption part 312 is stopped, the cartridge 112(114) is separated from the adsorption part 312, and the cartridge 112(114) is set on the treatment lane of the treatment part 110.

Note that the information memory 112c can be a QR code (registered trademark), a bar code, an IC tag, or the like. Information is preferably read by the information reading part 350 at the time of storing the cartridge into the sample storing unit 600 and/or at the time of taking the cartridge out of the sample storing unit 600. In the information memory of each cartridge, a treatment step in which the cartridge is usable, a lot and a use period of the cartridge, and some other information are stored. Preferably, the cartridge with its use period expired can be automatically transferred and disposed of by the cartridge picker into the consumable waste port 130. The information memory enables taking-out of an appropriate sample and/or cartridge at the time of conducting many types of tests and prevention of the sample and/or cartridge from being mixed up. The pickup unit 300 has been described as a unit obtained by integrating the cartridge transferring unit that transfers the cartridge with the specimen transferring unit that transfers a specimen (sample), but the cartridge transferring unit and the specimen transferring unit can also be provided independently of each other so as to be movable.

<Cartridge Fixing Mechanism>

Figure 13:
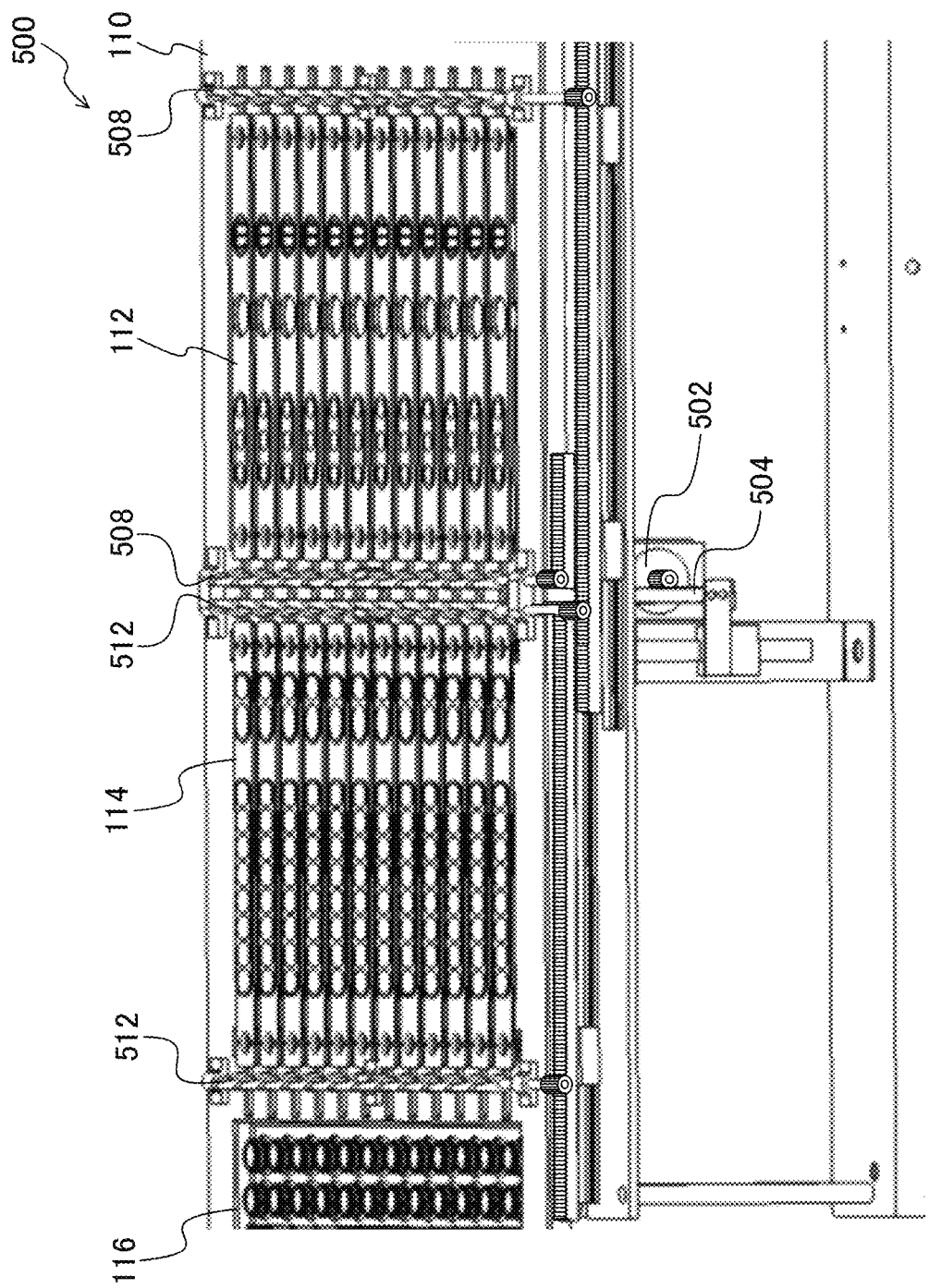
FIG. 13 is a perspective view of a non-fixed state of a cartridge fixing mechanism according to the first embodiment of the present invention.
Figure 14:
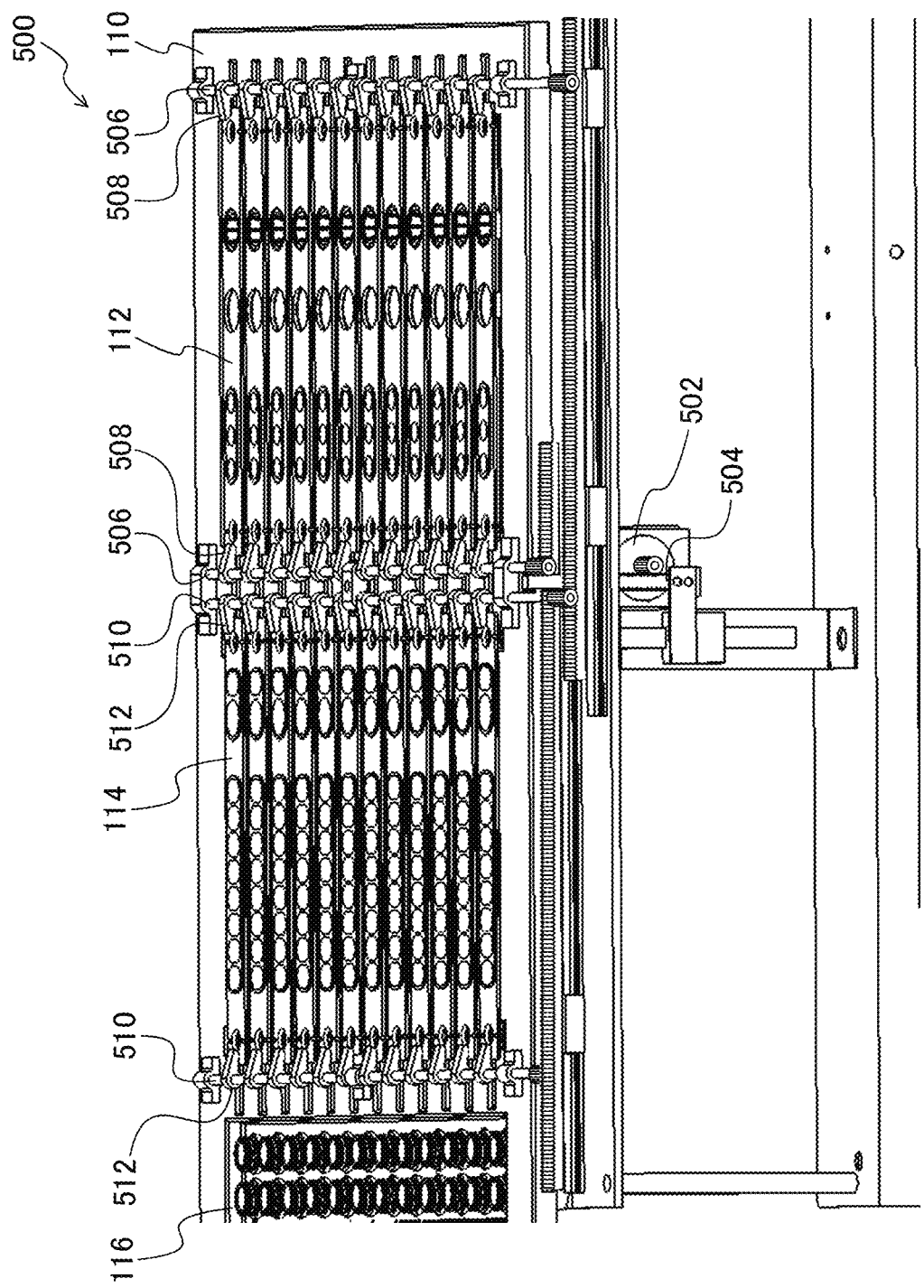
FIG. 14 is a perspective view of a fixed state of the cartridge fixing mechanism according to the first embodiment of the present invention.
Figure 15:
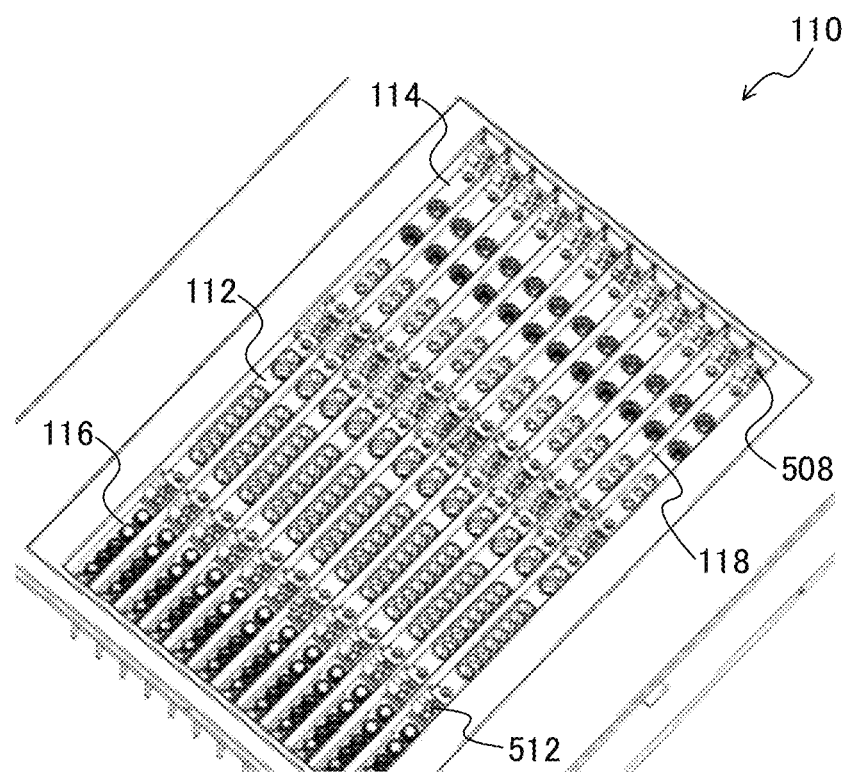
FIG. 15 is a perspective view of the cartridge fixing mechanism and partition walls according to the first embodiment of the present invention.
Figure 15:
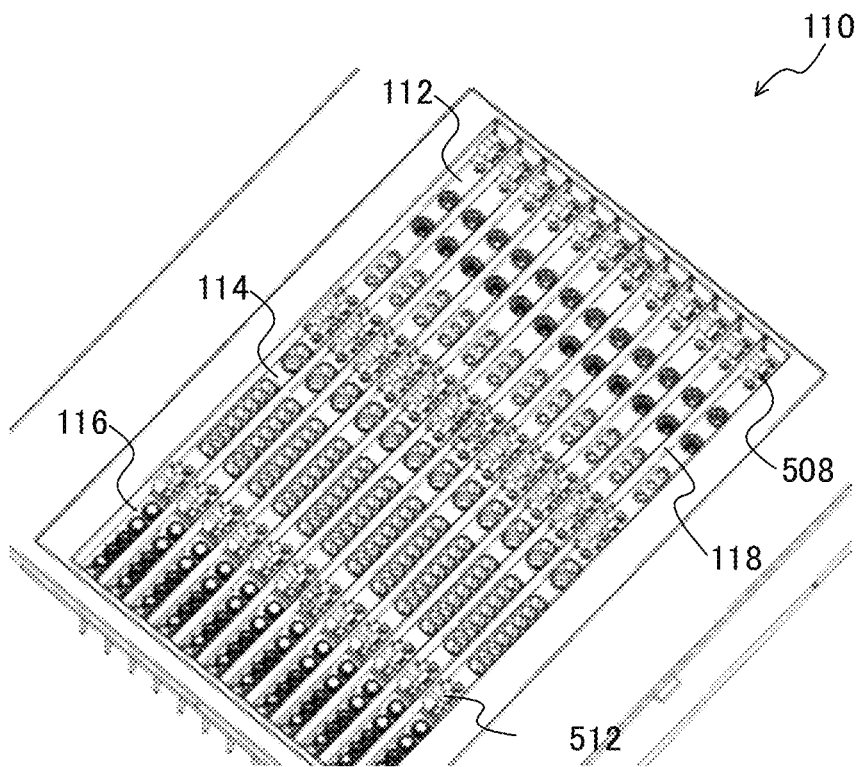

A cartridge fixing mechanism 500 will be described with reference to FIGS. 13 to 15. As shown in FIG. 13, in each of a plurality of treatment lanes of the treatment part 110, the cartridges 112, 114 are arranged in a non-fixed state by the cartridge fixing mechanism 500. The non-fixed state is a state before and after execution of the treatment. The cartridge fixing mechanism 500 is made up of: a motor 502; a gear mechanism 504 formed of a plurality of gears driven by the motor 502; a pair of first rotary shafts 506 arranged in the vicinity of both ends of the cartridge 112 and rotated by a gear mechanism 504; a plurality of first claws 508 rotated integrally with the first rotary shafts 506; a pair of second rotary shafts 510 arranged in the vicinity of both ends of the cartridge 114 and rotated by the gear mechanism 504; and a plurality of second claws 512 rotated integrally with the second rotary shaft 510.

In the state of FIG. 13, the tips of the first claws 508 and the second claws 512 face upward and are not holding the cartridges 112, 114. When the motor 502 is rotated in this state to drive the gear mechanism 504, the first claws 508 and the second claws 512 are rotated to come into a fixed state in which the first claws 508 and the second claws 512 hold both ends of each of the cartridges 112, 114 for fixation. FIG. 14 shows the fixed state during execution of the treatment. For releasing the fixed state, the motor may only be rotated in the opposite direction. Note that the gear mechanism 504 can rotate the first claw 508 and the second claw 512 by combination of a pinion gear and a rack gear. In the cartridge fixing mechanism 500 shown in FIGS. 13 and 14, both the cartridges 112, 114 are fixed simultaneously, but a first cartridge fixing mechanism for fixing the cartridge 112 and a second cartridge fixing mechanism for fixing the cartridge 114 can be provided. In this case, during execution of the treatment with the cartridge 112 being fixed by the first cartridge fixing mechanism, the fixation of the cartridge 114 having completed the treatment can be released and the cartridge 114 can then be transferred and disposed of by using the cartridge picker 310. As shown in FIG. 15, a partition wall 118 is provided between each lane of the treatment part 110. The partition wall 118 can facilitate arrangement of the cartridge on each lane and prevent contamination between each lane.

<Cartridge Storing Unit>

Figure 16:
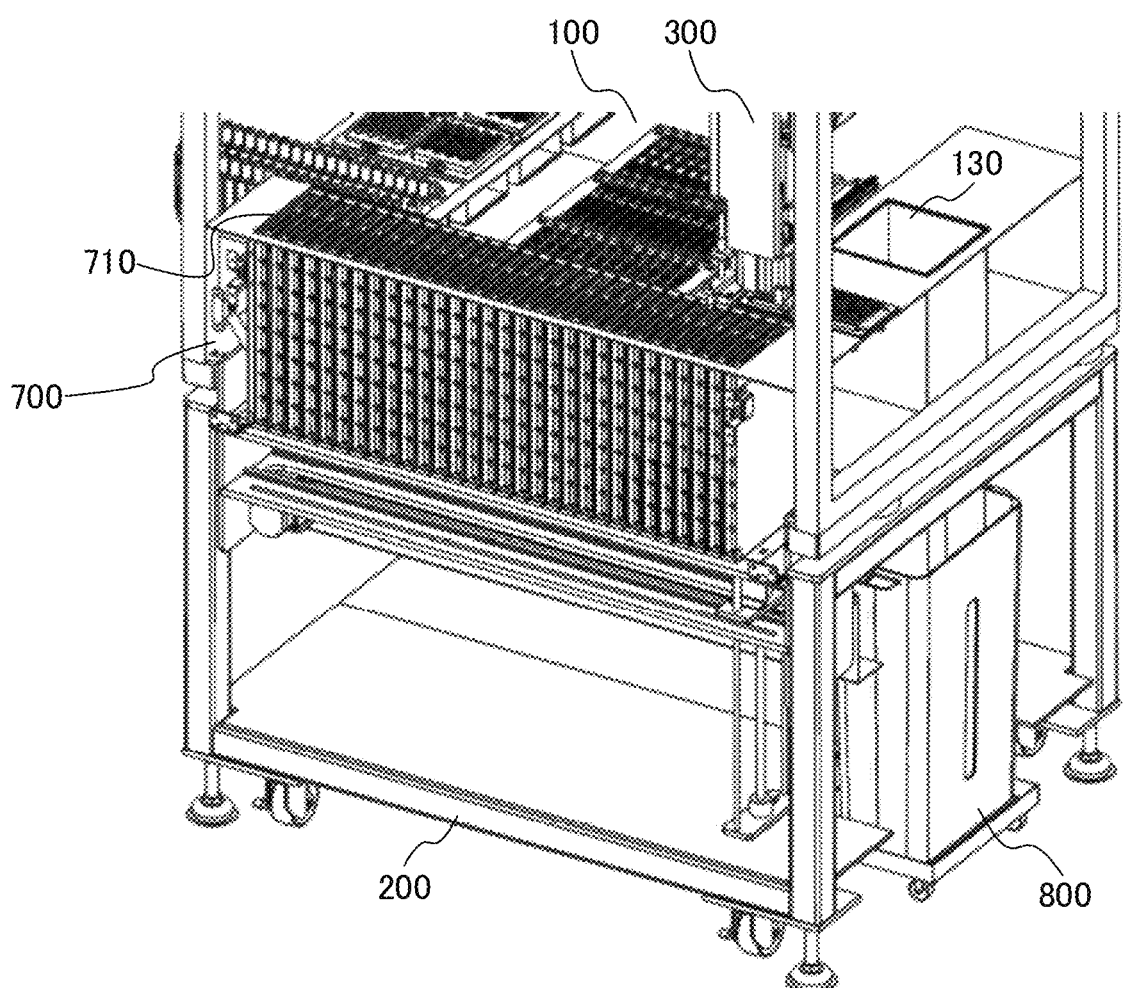
FIG. 16 is a perspective view of a cartridge storing unit according to the first embodiment of the present invention.
Figure 17:
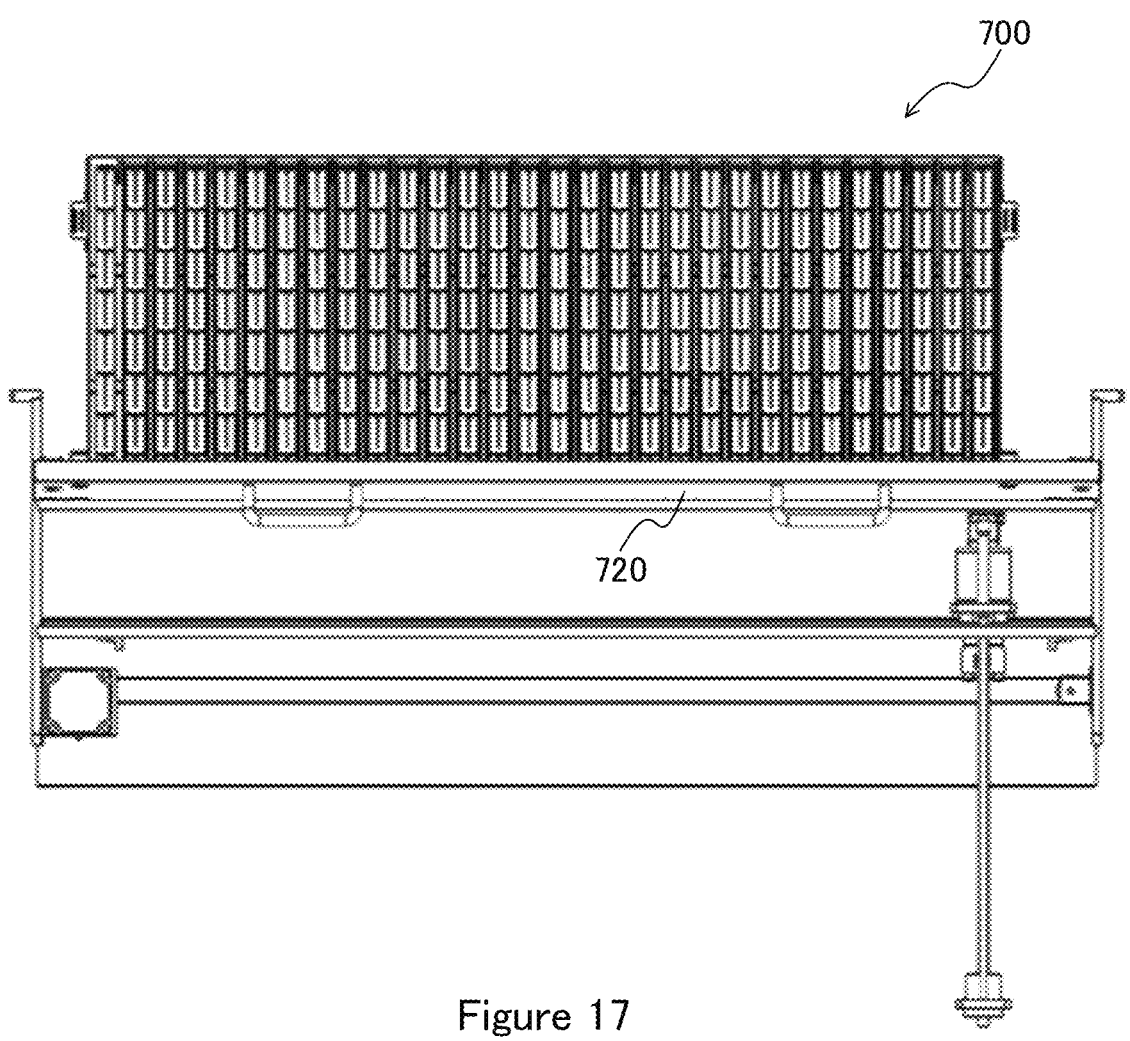
FIG. 17 is a front view of the cartridge storing unit of FIG. 16.
Figure 18:
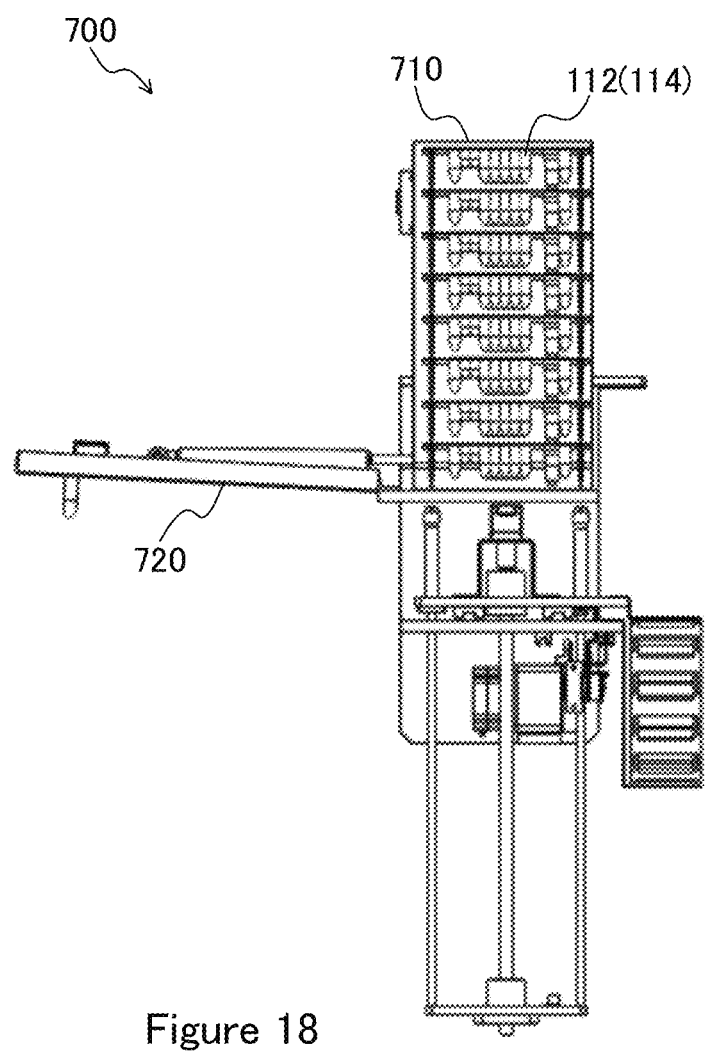
FIG. 18 is a side view of the cartridge storing unit of FIG. 17.

The cartridge storing unit (cartridge magazine lack unit) 700 will be described with reference to FIGS. 16 to 18. The cartridge storing unit 700 stores the plurality of cartridges 112, 114 in a laminated state. The cartridge outlet 710 is formed on the upper surface of the cartridge storing unit 700, and the plurality of cartridges 112, 114 are exposed in the cartridge outlet 710. A door 720 is provided on the side surface of the cartridge storing unit 700. The plurality of cartridges 112, 114 are urged upward while laminated, and when the top cartridge is taken out by using the cartridge picker 310, a cartridge immediately thereunder moves up to the takeout position. Hence the top cartridge is always kept at the same height.

<Flowchart>

Figure 19:
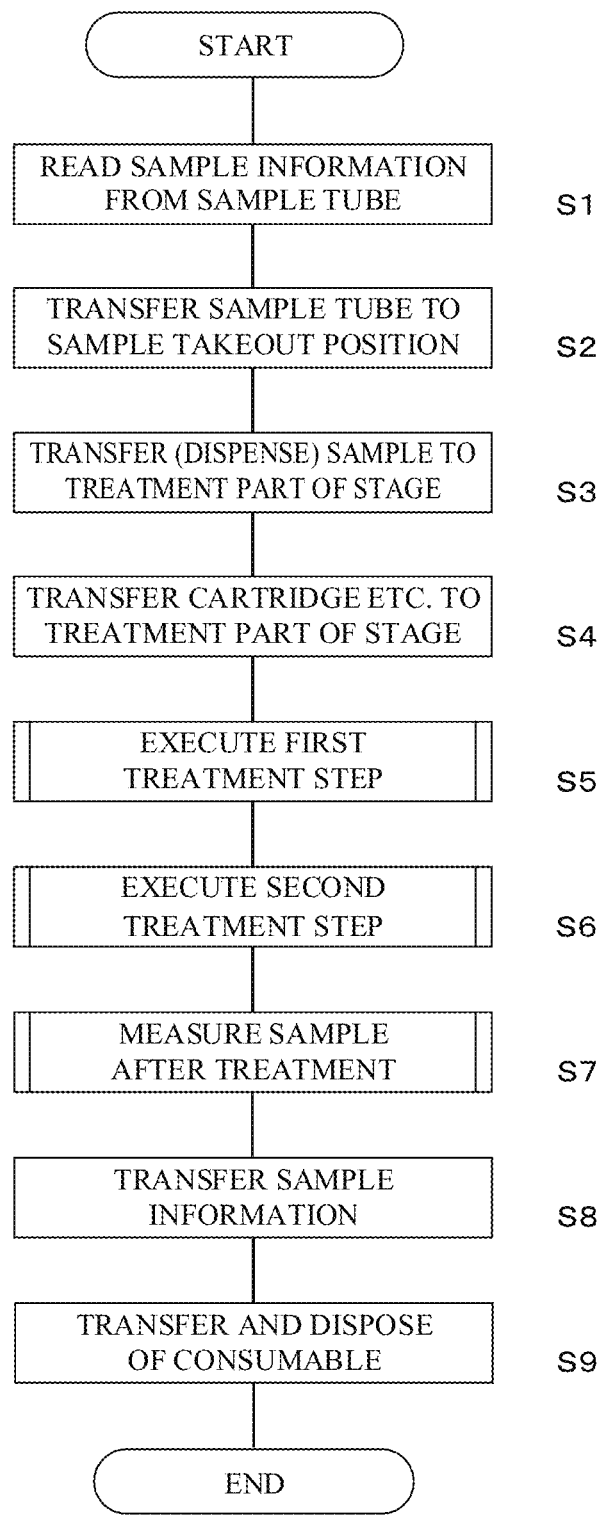
FIG. 19 is a flowchart according to the first embodiment of the present invention.

A flowchart of the specimen treatment and measurement system 1000 according to the first embodiment of the present invention will be described with reference to FIG. 19. The flowchart of FIG. 19 is not restrictive, but the use of the system in a large-scale hospital is assumed. In the specimen treatment and measurement system 1000 of the first embodiment of the present invention, it is preferably possible to conduct a gene test of DNA/RNA and the like, an immunological test, a biochemical test, and some other test. First, in the hospital, blood (whole blood) of a patient is collected using a vacuum blood collection tube, and the blood is tested in each test system including the specimen treatment and measurement system 1000. At the time of conducting this test, a rubber stopper of the vacuum blood collection tube is removed so that the vacuum blood collection tube can be supplied as a sample tube to an automatic test system of the present invention. Alternatively, without removing the rubber stopper, blood can be sucked from the vacuum blood collection tube by using a needle attached to the nozzle part 320 of the pickup unit 300. In the automatic test system according to the first embodiment of the present invention, a cartridge (information management) provided with a prefilled reagent and solution, and the like can preferably be coupled with a cartridge auto-loading system and a multi-item detection mechanism such as a gene LEAD (Precision System Science Co., Ltd.) and a biochemical testing unit. This enables construction of a system with a completely new concept, taking advantages of the multi-sample batch system and the one-sample random access system.

The flowchart of FIG. 19 is as follows: In step S1, sample information is read from a sample tube. The sample information is stored in the information memory 608 (FIG. 7) of a bar code, an IC chip, or the like, attached to the tube holder 604 or the sample tube 606, and read by the information reading part 610 (FIG. 7) or the information reading part 350 (FIG. 9). In step S2, the sample tube 606 is transferred to the takeout position (sucking position) 612 (FIG. 7) by using the chain conveyer 602 of the sample storing unit 600. In step S3, the nozzle part 320 of the preparing movement unit 300 sucks the sample and dispenses the sample to a tube for treatment in the treatment part 110. In step S4, the cartridge, the dispensation chip, and the like conforming to the treatment items are transferred to each lane of the treatment part 110 of the stage 100 by using the cartridge picker 310 (loading arm) or the consumable picker 330 in the preparing movement unit 300.

In step S5, a first treatment step (extraction step) is executed. The first treatment step is, for example, DNA/RNA extraction using a magnetic body and an extracted reagent, for example, and executed by the extraction cartridge 112 (extraction functioning part). Operation steps of all the treatment steps can be automated. The DNA extraction step is executed by using the dispensation nozzle of the treatment executing unit 400 to perform suction, discharge, and the like on each well of the cartridge 114. In the DNA extraction step, firstly, a cell is lysed to expose DNA therefrom (give a dissolved buffer solution), followed by heating. Secondly, the DNA is mixed with a magnetic particle solution, and a magnet is attached to and separated from the container and the dispensation chip (cf. FIG. 3 of Patent Literature 1, and Non Patent Literature 1). Thirdly, the DNA coupled with the magnetic particle is separated from the solution by the magnet, and then subjected to capture, stirring, suction, and discharge by using the dispensation nozzle and the well. Fourthly, the DNA is separated from the magnetic body (to give a DNA extracted buffer solution), and the magnet is attracted to and separated from the container and the dispensation chip. Finally, a DNA refined solution is obtained to complete the first treatment step. The DNA refined solution is transferred to the cartridge 114 (amplification and measurement functioning part) of a second treatment step (amplification step).

In step S6, the second treatment step is executed. The second treatment step is executed by using a plurality of dispensation nozzles (nozzle parts) of the treatment executing unit 400 to perform suction, discharge, and the like on each well of the second cartridge 114. Specifically, the refined DNA is amplified and measured (real time PCR) in the following manner: Firstly, stirring/suction and discharge of the DNA refined solution and PCR reagents are controlled so as to disperse and mix the DNA refined solution and PCR reagents. The PCR reagent is dNTP (DNA amplified container), Primer, a buffer, or the like. Secondly, the PCR container is capped or sealed using the dispensation nozzle of the treatment executing unit 400. Thirdly, heating and cooling treatment is repeatedly performed by a thermal cycler to execute PCR and amplify the DNA.

In step S7, the measurement unit 900 is used to execute a detection step for a sample being in the second treatment step or a sample having completed the amplification. In the real time PCR, steps S6 and S7 are executed simultaneously. The measurement unit 900 performs real time measurement of the amplified DNA to analyze a fluorescent amount and a fluorescent curve. Specifically, irradiation with excitation light of six colored fluorescent material and filtering of wavelengths are performed using an optical unit of the measurement unit 900 to receive fluorescence. In step S8, detection information (diagnosis information, etc.) is acquired and transmitted to a host server of the hospital or the like. Finally, in step S9, each used consumable is disposed of from the stage into the consumable waste port 130 to terminate the treatment step.

As illustrated in FIG. 3, at the time of combining the multi-sample batch system and the one-sample random access system, there occurs a big problem due to many types of tests being conducted, namely, a problem where not only many types of reagent bottles are needed, but the step of dispersing a plurality of reagents becomes complex. Therefore, in the first embodiment of the present invention, by using the prefilled cartridge, obtained by previously dispensing, pre-packing, and sealing many types of reagents and/or solutions into the "cartridge provided with a plurality of wells", it has been possible to eliminate the need for the complicated dispensation step and preparation of the reagent bottles. Further, each one of the cartridges can be provided with the information memory 608, 112c of a QR code (registered trademark), a bar code, an IC chip, or the like.

Then, a plurality of cartridges 112, 114 are arrayed on the plurality of lanes of the treatment part 110. In the specimen treatment and measurement system 1000, the information reading part 350 or 610 reads information (QR code (registered trademark), bar code, IC chip, etc.) of a specimen sent at random from the information memory 608 provided on the sample tube, and the random access treatment as a whole can be performed based on the read information. Based on this sample information, the plurality of samples are segmented in an arrangement, where the batch treatment can be performed, and the batch treatment is executed on a plurality of samples by using multiple string dispensation nozzles of the treatment executing unit 400. In the first embodiment of the present invention, it has been possible to build a highly rational test system by combining the batch treatment and the specimen random access treatment.

The features of the first embodiment of the present invention are as follows:

The pickup unit 300 (FIGS. 4, 8, and 9) including the movement mechanism is provided, the mechanism being movable three-dimensionally above the stage. The multiple alignment and the lifting and lowering transfer (FIG. 12) can be achieved by the cartridge picker 310 of the pickup unit 300.

The auto-loading mechanism (the cartridge picker 310 of the pickup unit 300) is provided, where the consumables of the prefilled cartridges 112, 114, the dispensation chip, and the like are automatically transferred to and arranged in the treatment part 110 that performs the batch treatment. The auto-loading mechanism is achieved by the cartridge picker 310 (FIGS. 9 and 11) of a vacuum adsorption system not requiring a complex configuration.

The dispensation mechanism (the nozzle part 320 of the pickup unit 300) is provided to perform specimen dispensation and dispensation to the cartridges 112, 114.

The information system (information memories 608, 112c, and information reading parts 350, 610) is provided to read information of a reagent and a specimen.

The specimen treatment and measurement system according to the first embodiment of the present invention has made it possible to perform transfer of a cartridge from the storage functioning part (cartridge storing unit 700) to each treatment functioning part (each treatment lane of the treatment part 110), dealing with a consistent multi-item test by random batch treatment on specimen information, and continuous access treatment which has been difficult for the conventional batch treatment system. Further, it has been possible to ensure improvement in stability of a test result, cost reduction, space saving, and operation easiness by fixing and simplifying a reaction functioning part (cartridge) (use of a prefilled cartridge).

In the first embodiment of the present invention, the cartridges 112, 114 installed on the treatment part 110 can preferably execute the treatment step without moving from the region of the treatment part 110. In the first embodiment of the present invention, it is preferably possible to perform treatment on a plurality of samples (12 samples in the first embodiment) simultaneously in parallel only by a plurality of dispensation nozzles of the treatment executing unit 400 performing the same sucking and discharging operation on many rows of treatment lanes provided in the treatment part 110 at the time of treatment. It is thereby possible to achieve the batch treatment system. In the first embodiment of the present invention, it is preferably made possible to simultaneously perform some types of random samples (requiring different types of treatment) in parallel in the same manner by devising reagents. For example, it is possible to perform treatment on a serum sample and whole blood sample in the same protocol (sucking, discharging and moving operation of the dispensation nozzle) despite reagents being different. In the first embodiment of the present invention it is preferable to prepare a plurality of basic protocols (common protocols) and make division into a plurality of groups each only including one on which treatment can be performed in the same protocol. Then, one group is used for one-time pretreatment, so that one-time treatment operation can be made uniform to enable parallel treatment. In this case, a necessary reagent can be used in the same protocol. This enables the treatment to be performed in a continuous and endless manner, thus leading to improvement in throughput or operation rate of the specimen treatment and measurement system.

In the first embodiment of the present invention, it is preferably possible to attach a rubber stopper (rubber lid) piercing needle (piercing chip) to the single nozzle (nozzle part 320) of the pickup unit 300. With the sample tube 606 taken as the vacuum blood collection tube (sample tube) that includes the rubber stopper, it is also possible to pierce (punch) the rubber stopper with the needle attached to the nozzle part 320, and to suck a sample from the sample tube 606. In the first embodiment of the present invention, the extracted solution of DNA or the like obtained from the pretreatment step can preferably be transferred to and stored into the tube of the extract etc. storing rack 140 at a request by using the nozzle part 320 of the pickup unit 300.

In the first embodiment of the present invention, it is preferably possible to separate and dispose of consumables of a used cartridge, a dispensation chip, a sample tube, and the like. For example, when the consumable is disposed of by using each of the pickers 310, 330 of the pickup unit 300 after the treatment step has been terminated, the consumable waste port 130 is formed into a plurality of separating waste ports so that a separating waste bag can be connected to each separating waste port. It is thereby possible to separately dispose of the consumable.

Second Embodiment

<Summary of Specimen Treatment and Measurement System>

Figure 20:
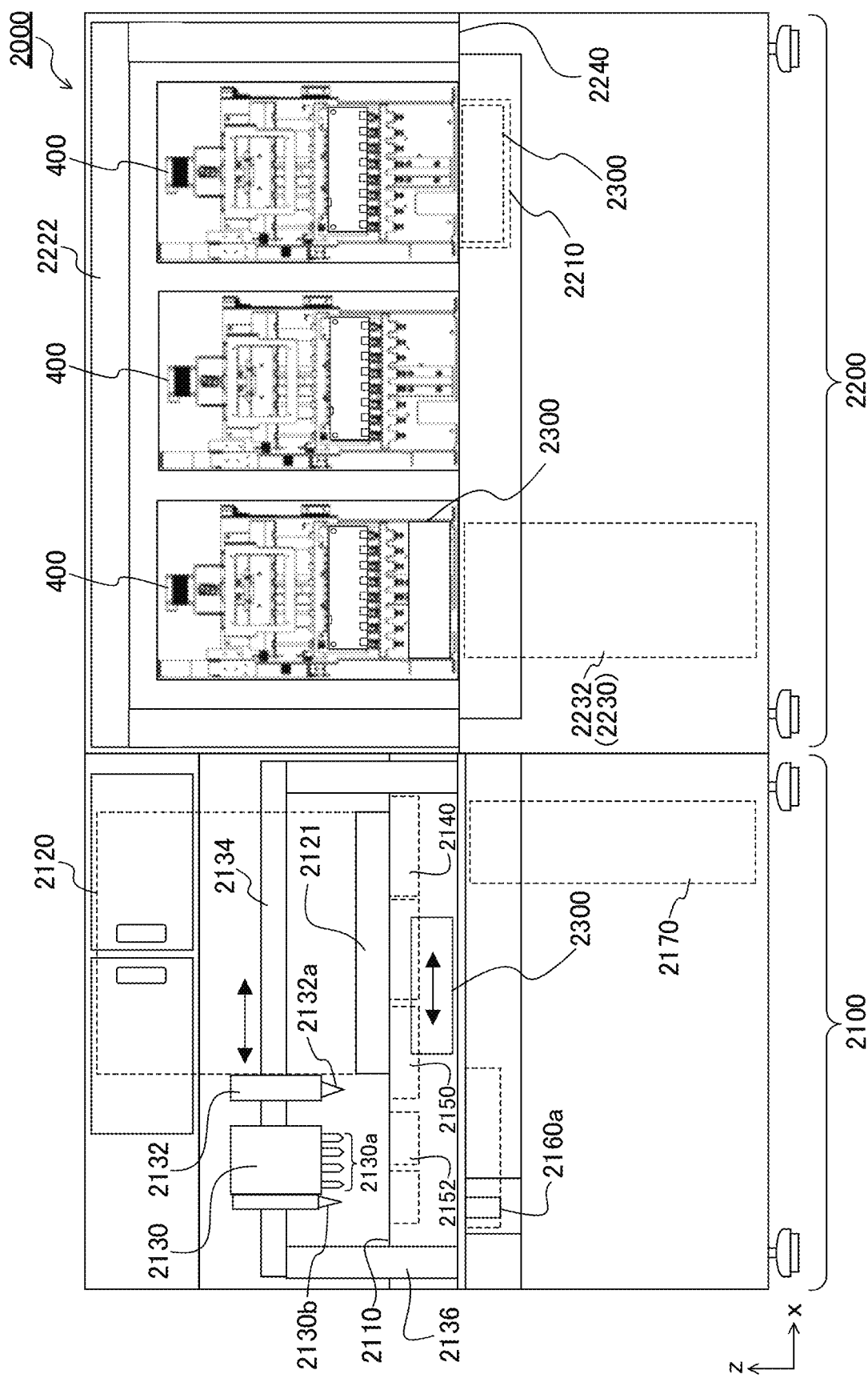
FIG. 20 is a front view of a specimen treatment and measurement system according to a second embodiment of the present invention.
Figure 21:
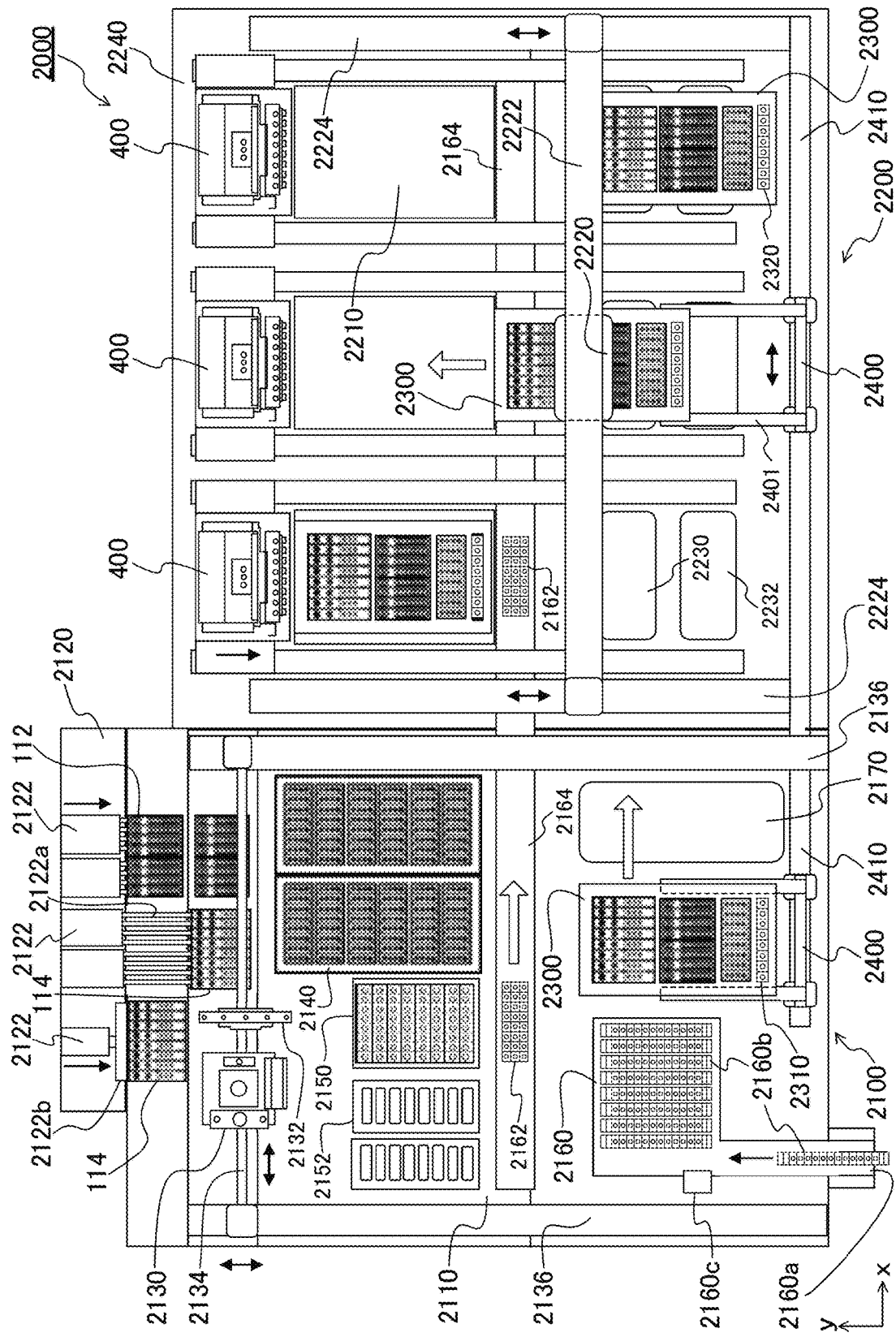
FIG. 21 is a top view of the specimen treatment and measurement system of FIG. 20.

A specimen treatment and measurement system 2000 according to a second embodiment of the present invention will be described. As shown in FIGS. 20 and 21, the specimen treatment and measurement system 2000 includes: a treatment preparation sub-system 2100; a treatment execution sub-system 2200; a plurality of movable stage racks (movable stages) 2300; and a stage-rack transferring mechanism 2400 that transfers the plurality of stage racks 2300 between the treatment preparation sub-system 2100 and the treatment execution sub-system 2200. A consumable and the like are placed or installed on the stage rack 2300 on the treatment preparation sub-system 2100 side. The stage racks 2300 on which the consumable and the like are placed are mounted in the plurality of treatment executing units 400 having been transferred to the treatment execution sub-system 2200 side and assembled into the treatment execution sub-system 2200. The treatment executing unit 400 executes treatment (extraction, amplification, and measurement) on a plurality of specimens accommodated in a specimen container of the stage rack 2300 along a plurality of treatment lines provided on the stage rack 2300.

<Treatment Preparation Sub-System>

As shown in FIG. 21, the treatment preparation sub-system 2100 includes a treatment preparation stage 2110 that stores various consumables, and a cartridge supplying unit 2120 that supplies the cartridge to the treatment preparation stage 2110. The treatment preparation stage 2110 includes thereabove a pickup unit 2130 and a cartridge picker (air pin set) 2132 in a three-dimensionally movable manner. Further, the treatment preparation stage 2110 includes a consumable storing unit 2140 that stores a consumable of a dispensation chip, a piercing chip, or the like, a container storing part 2150 that stores containers for various reagents such as a PCR reagent and/or an additional specimen container, a reagent storing part 2152 that stores various reagents such as the PCR reagent, and a main specimen storing part 2160 that stores a main specimen. The consumable storing unit 2140 accommodates a consumable of any of a large capacity dispensation chip, a small capacity dispensation chip, a piercing chip for piercing an aluminum sealing of a sealed container, and a PCR well sealing lid, for example. The main specimen storing part 2160 and/or the reagent storing part 2152 can preferably be provided with a temperature adjusting mechanism (cooling mechanism) that adjusts a temperature of (cools) a main specimen and/or a reagent.

The cartridge supplying unit 2120 is placed adjacent to the treatment preparation stage 2110 and extends upward from the treatment preparation stage 2110. The cartridge supplying unit 2120 supplies the extraction cartridge 112, the PCR cartridge 114, an integrated type cartridge 113 (FIG. 29), and the like toward the treatment preparation stage 2110. The cartridge supplying unit 2120 is provided with a cartridge push-out mechanism 2122 (FIG. 21) that pushes a plurality of bottom cartridges out of a cartridge supply port 2121 (FIG. 20) toward the treatment preparation stage 2110. The cartridge push-out mechanism 2122 can be provided with a plurality of push-out pins 2122*a* that expands and contracts with an actuator such as a solenoid, a hydraulic cylinder, or the like. The operation of the cartridge push-out mechanism 2122 is driven by the controller, not shown. The cartridge push-out mechanism 2122 has been assumed to be provided with one push-out pin 2122*a* for one cartridge, but can also be provided with a push-out plate 2122*b* that pushes out a plurality of cartridges at once.

As shown in FIG. 20, the pickup unit 2130 can be provided with one or a plurality of (e.g., quadruplet) consumable pickers 2130*a* and at least one dispensation nozzle 2130*b*. The cartridge picker 2132 includes a pair of adsorption parts (protrusions) 2132*a* that movably adsorb both ends of the cartridge 112(114) or 113. The adsorption part 2132*a* projects in a conical shape and its tip is provided with an opening. The opening of the adsorption part 2132*a* is connected to the vacuum pump, not shown. The pickup unit 2130 and the cartridge picker 2132 are each provided with a motor for movement in the x-direction and is individually movable in the x-direction along a first rail 2134. The first rail 2134 is movable in the y-direction above a second rail 2136 by a motor for movement in the y-direction. A consumable picker 2130*a* and a dispensation nozzle 2130*b* of the pickup unit 2130 are each provided with a motor for lifting and lowering in the z-direction and can independently move up and down in the z-direction. Hence the pickup unit 2130 and/or the cartridge picker 2132 can place a consumable and the like in predetermined positions on the stage rack 2300 from the consumable storing unit 2140. Note that the treatment preparation sub-system 2100 can also be provided with the pickup unit 300 (FIGS. 8 to 10) obtained by integrating the pickup unit 2130 and the cartridge picker 2132 instead of being provided with each of those.

A plurality of main specimens (e.g., vacuum blood collection tubes) are stored in the main specimen storing part 2160. The main specimen is put on a main specimen tray 2160*b* and carried in from a specimen carrying-in part 2160*a*. The main specimen tray (elongated rack) 2160*b* preferably accommodates 12 main specimen containers. The main specimen storing part 2160 accommodates eight main specimen trays 2160*b* and can thus accommodate the total of 96 main specimens. Each of the individual main specimen containers is provided with an information memory of a bar code or the like. An information reading part 2160*c* provided in the main specimen storing part 2160 reads specimen information from the information memory. In the information memory, any of the following is recorded as specimen information: a specimen number, a specimen collected date, a place of collection (hospital ward name), a doctor in charge, information on a patient having provided the specimen, an urgent specimen or not, an infectious disease to be tested, and the like.

The stage-rack transferring mechanism 2400 can transfer the stage rack 2300 in the x-direction along a rail 2410 by using the motor for transfer in the x-direction. The treatment preparation stage 2110 can preferably be provided with a slide rack (transport container) 2162 including a plurality of wells or containers. The slide rack 2162 is movable between the treatment preparation sub-system 2100 and the treatment execution sub-system 2200 along a slide rail 2164. The slide rail 2164 extends in the x-direction between the treatment preparation sub-system 2100 and the treatment execution sub-system 2200, and the slide rack 2162 is moved by the slider and a motor for the slider (slide mechanism).

The treatment preparation sub-system 2100 further includes a cartridge waste box 2170. The cartridge waste box 2170 is adjacent to the stage rack 2300 having moved to the consumable installed position and is placed at a position lower than the stage rack 2300. The used cartridge is disposed of into the cartridge waste box 2170 by using the cartridge picker 2132.

<Treatment Execution Sub-System>

As shown in FIG. 21, the treatment execution sub-system 2200 includes a treatment execution stage 2240, a plurality of treatment executing units 400 set on the treatment execution stage 2240, a plurality of stage-rack mounting parts 2210 that respectively install a plurality of stage racks 2300 on the treatment execution stage 2240, and a stage-rack mounting mechanism 2220 that transfers the stage rack 2300 on the treatment execution sub-system 2200 side to the stage-rack mounting part 2210 to be mounted thereon.

The stage-rack mounting mechanism 2220 is three-dimensionally movable above the treatment execution stage 2240. The stage-rack mounting mechanism 2220 is attached to the rail 2222 extending in the x-direction and movable in the x-direction by the motor for movement in the x-direction. The rail 2222 is movable in the y-direction along a rail 2224 extending in the y-direction. The stage-rack mounting mechanism 2220 includes a pair of openable arms (not shown) carrying the stage rack 2300, and the arms can be lifted and lowered in the z-direction by the motor for lifting and lowering in the z-direction. The stage-rack mounting part 2210 includes a lifting adhering mechanism (not shown) that lifts and lowers the stage rack 2300 while being mounted with the stage rack 2300. After the stage rack 2300 has been mounted on the stage-rack mounting part 2210, the stage rack 2300 is lowered by the lifting adhering mechanism, and a heat block for PCR is caused to adhere to a PCR well of the PCR cartridge 114 or the integrated type cartridge 113 placed on the stage rack 2300.

In the treatment execution sub-system 2200, in front of the treatment execution stage 2240, below the region where the stage rack 2300 moves in the x-direction, there are provided a consumable waste box 2230, and a waste liquid tank 2232. The consumable (used dispensation chip, etc.) removable from the dispensation nozzle is moved to above the consumable waste box 2230 in a state where the consumable is mounted in the dispensation nozzle provided in the treatment executing unit 400. Thereafter, the consumable is removed (pushed out) from the dispensation nozzle by the consumable removing mechanism provided in the dispensation nozzle and disposed of into the consumable waste box 2230. Similarly, the waste liquid is moved to above the waste liquid tank 2232 in a state where the consumable is sucked by the dispensation nozzle provided in the treatment executing unit 400. Thereafter, the waste liquid is discharged from the dispensation chip and disposed of into the waste liquid tank 2232.

<Stage Rack>

Figure 22A:
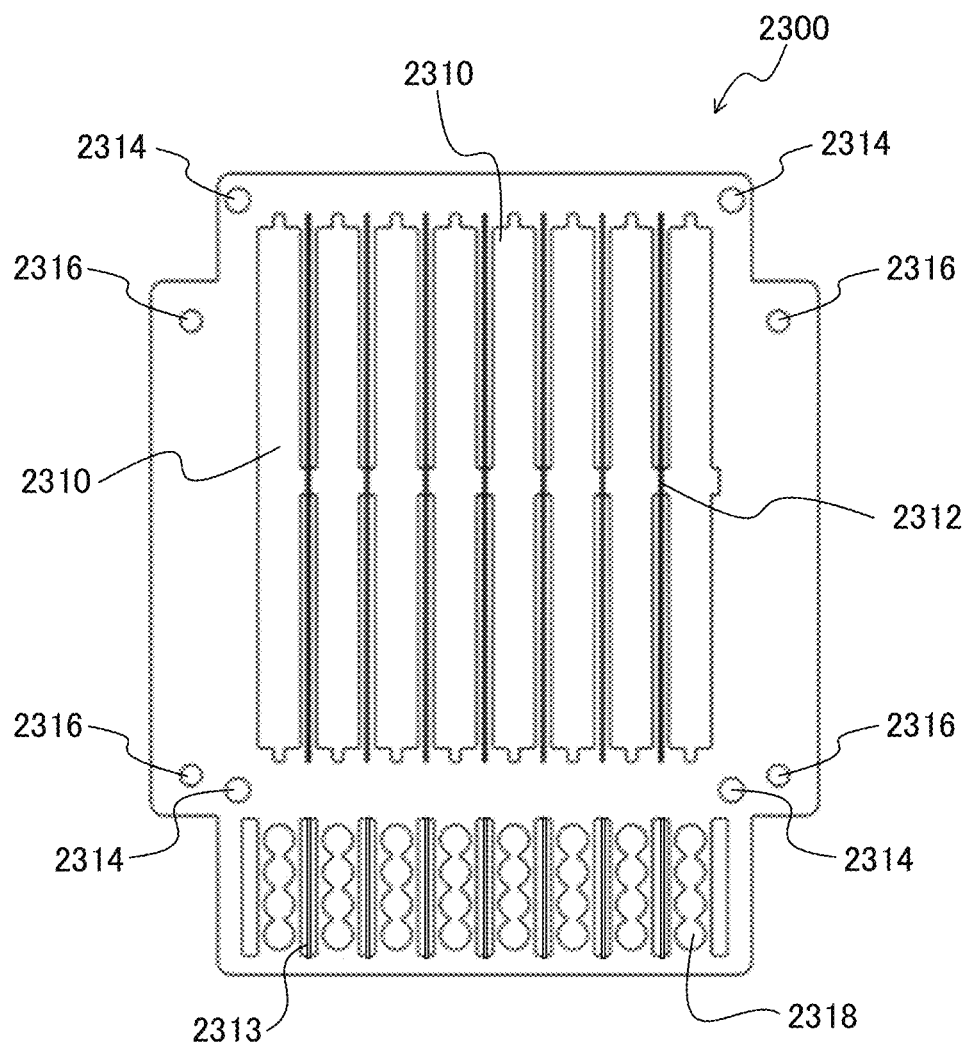
FIG. 22(a) is a top view.
Figure 22:
FIG. 22(b) is a front view.
FIG. 22(c) is a side view of a stage rack according to the second embodiment of the present invention.
Figure 22:
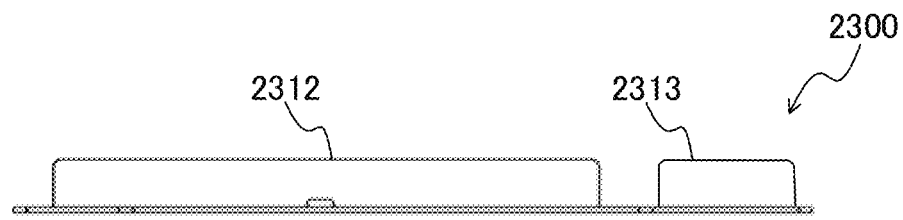
Figure 23:
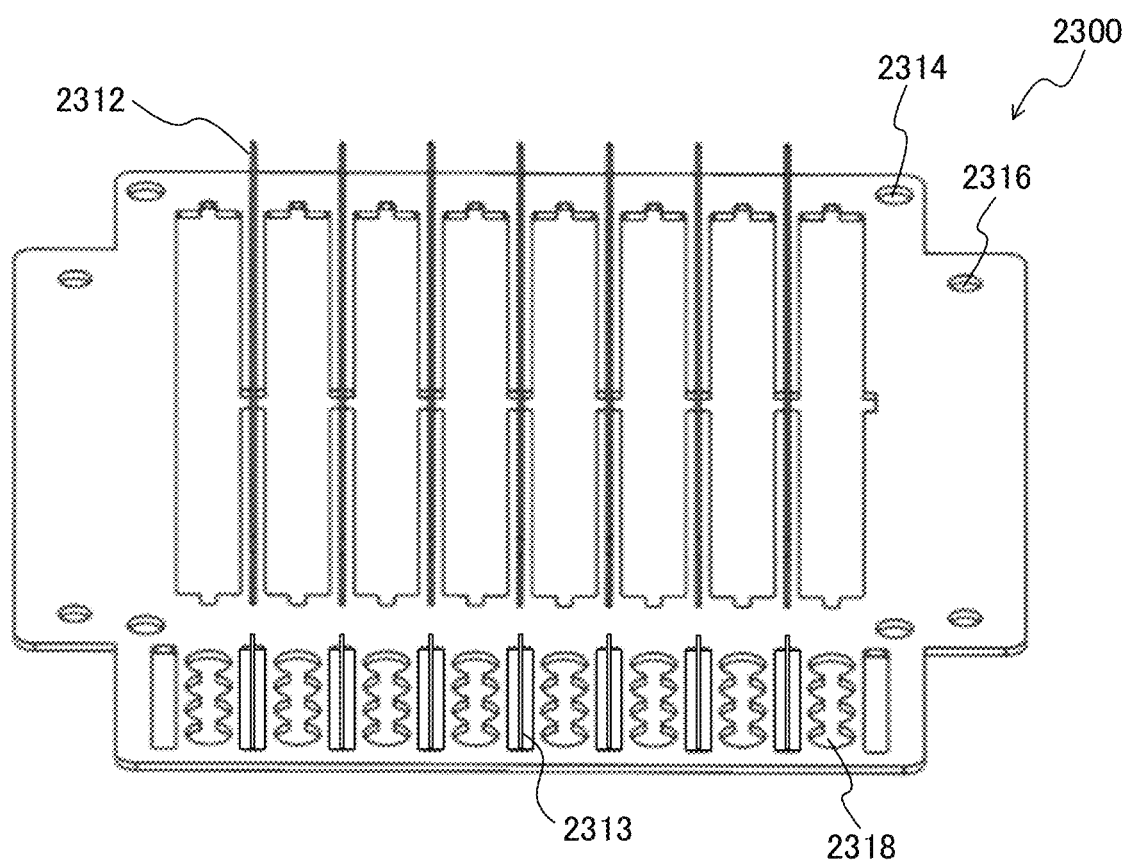
FIG. 23 is a perspective view of the stage rack of FIG. 22.

As shown in FIG. 22, the stage rack (movable stage) 2300 has a substantially flat shape and includes a plurality of treatment lanes 2310 arranged in parallel to each other, and an elongated tube accommodating part 2318 corresponding to each treatment lane. On each treatment lane, the extraction step (extraction function) and the amplification measurement step (amplification measurement function) are independently executed on an individual specimen. On the treatment lane 2310, a position of an extraction functioning part for executing the treatment step and a position of an amplification measurement functioning part for performing the amplification measurement step are fixed. In the tube accommodating part 2318, an additional specimen and/or a reagent tube 119 (FIG. 26) are accommodated. A partition wall 2312 projecting upward in parallel with each treatment lane 2310 is provided between each treatment lane 2310. A partition wall 2313 projecting upward in parallel with the tube accommodating part 2318 is provided between each tube accommodating part 2318. The partition walls 2312, 2313 can prevent contamination of a specimen on which treatment is performed on each treatment lane.

Figure 26:
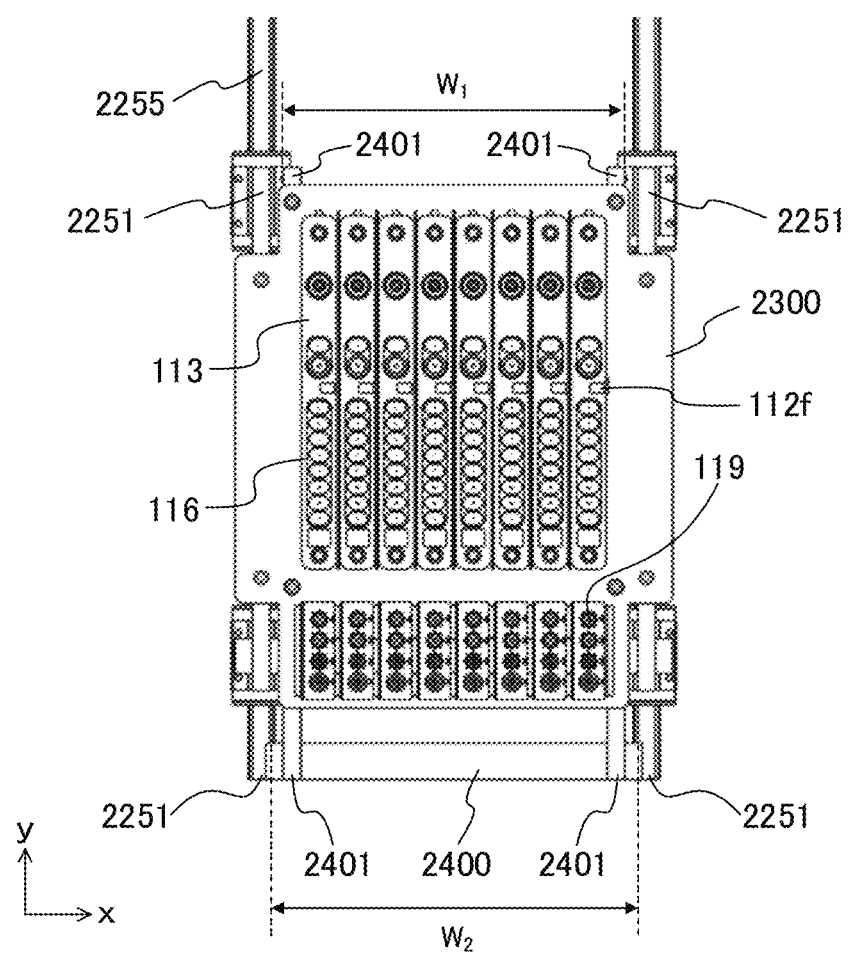
FIG. 26 is a plan view showing mounting of the stage rack on the stage rack mounting mechanism of FIG. 24.

The stage rack 2300 further includes a plurality of transferring connection holes 2314 and a plurality of mounting connection holes 2316. A plurality of transferring projections 2402 (FIGS. 24 and 27) of the stage-rack transferring mechanism 2400, described later, are inserted into the plurality of transferring connection holes 2314. A plurality of mounting projections 2252 (FIGS. 24 and 27) of a stage-rack mounting mechanism 2250, described later, are inserted into the plurality of mounting connection holes 2316. Four transferring connection holes 2314 and four mounting connection holes 2316 can preferably be provided, but the number of the holes is not limited to four, but may at least be two or larger. On each treatment lane 2310, as shown in FIG. 26 and the like, the additional specimen tube 119, the extraction cartridge 112, the PCR cartridge 114, the integrated type cartridge 113, and the like are placed.

<Cartridge Fixing Mechanism>

The stage rack 2300 includes a cartridge fixing mechanism (recessed groove part and pin) so as to fix the extraction cartridge 112, the PCR cartridge 114, or the integrated type cartridge 113. The case of providing the recessed groove part in the integrated type cartridge 113 will be described below, but the recessed groove part can also be provided in the same manner in the extraction cartridge 112 and the PCR cartridge 114. The integrated type cartridge 113 is obtained by integrating the extracted cartridge and the PCR cartridge, and can be made up of a DNA extracting part 133A and a PCR reacting part 113B as shown in FIG. 29.

Figure 29:
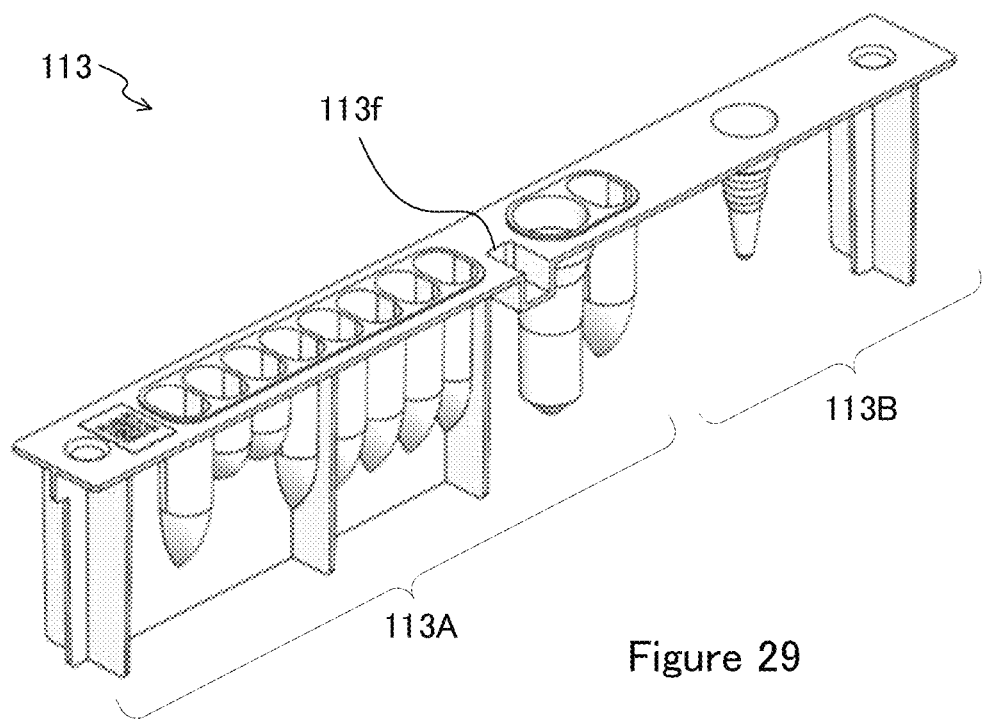
FIG. 29 is a perspective view of a cartridge for use in the second embodiment of the present invention.
Figure 30:
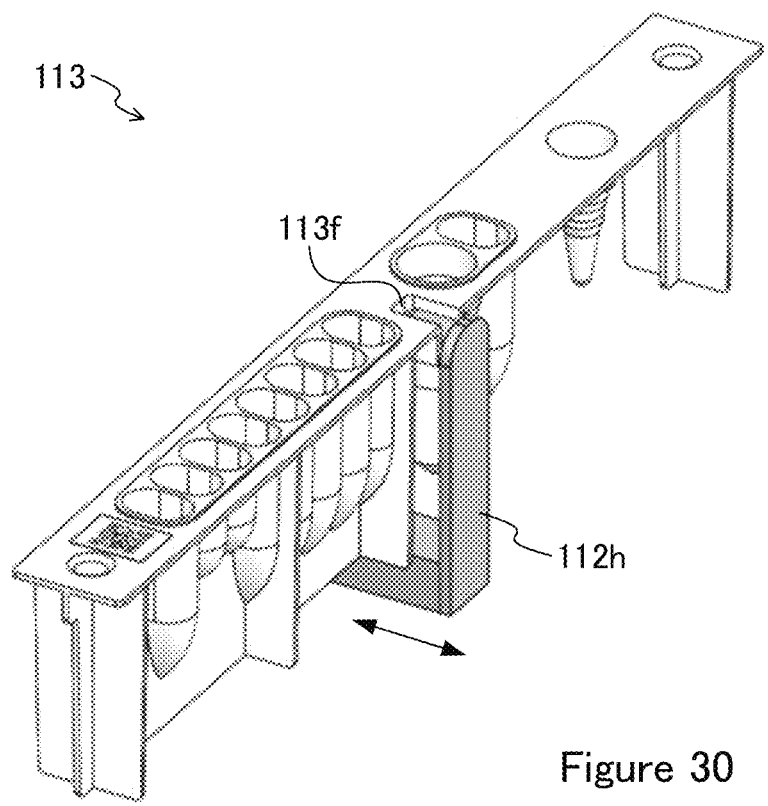
FIG. 30 is a perspective view showing a fixing mechanism of the cartridge of FIG. 29.
Figure 31:
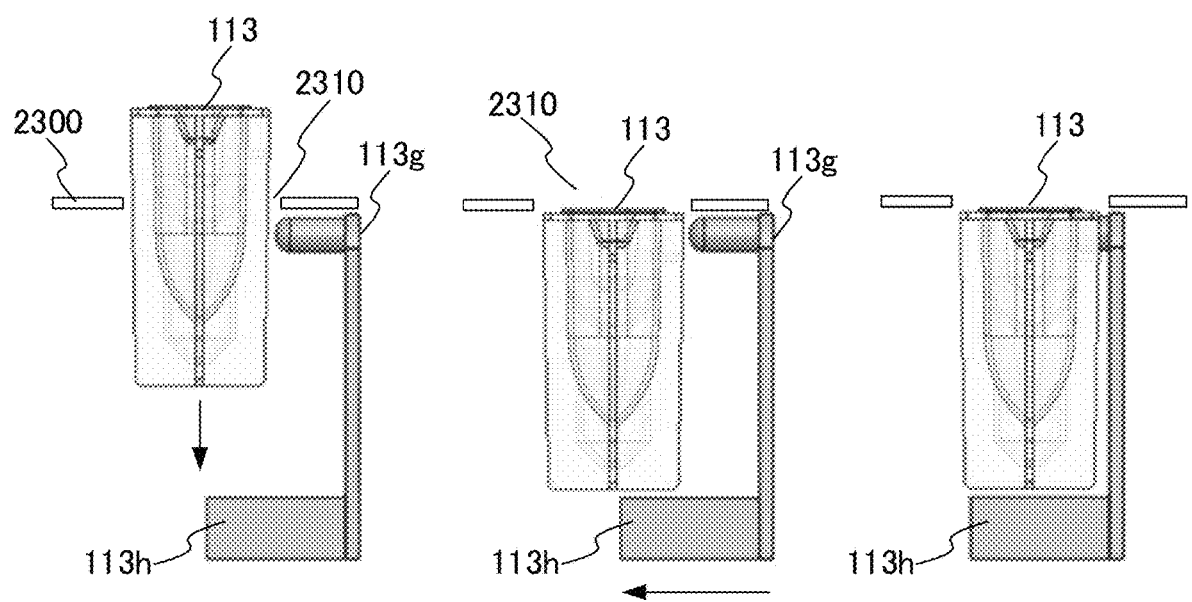
FIGS. 31(a) to 31(c) are side views showing operation of the fixing mechanism of the cartridge of FIG. 30.

As shown in FIGS. 29 and 30, the integrated type cartridge 113 includes, near the central part thereof, one recessed groove part (pin insertion part) 113f so as to be orthogonal to the longitudinal direction of the cartridge. As shown in FIGS. 30 and 31, the fixing mechanism includes a pin 113g that is inserted into and removed from the recessed groove part 113f in the direction of the side surface of the cartridge 113, and a pin supporter 113h that movably supports the pin 113g. FIGS. 29 and 31(c) are states in which the pin 113g has been inserted into the recessed groove part 113f. As shown in FIG. 31(a), the cartridge 113 (112, 114) is lowered from above toward the treatment lane 2310 of the stage rack 2300 by the cartridge picker 2132 (FIG. 20), and as shown in FIG. 31(b), the cartridge 113 (112, 114) is installed at a fixed position on the treatment lane 2310. Thereafter, as shown in FIGS. 31(c) and 29, the pin 113g is inserted into the recessed groove part 113f and the cartridge 113 is fixed. By fixing the cartridge 113 of FIGS. 31(c) and 29, the cartridge 113 is prevented from rising and falling off when the stage rack 2300 is transferred and mounted. The pin 113g and the pin supporter 113h are placed below the adjacent cartridge, and the pin supporter 113h is slid by an actuator provided on the stage rack 2300 or the like. This cartridge fixing mechanism (recessed groove part 113f, pin 113g, and pin supporter 113h) can also be configured such that a pair of recessed groove parts are provided at longitudinally both ends of the cartridge and the pin is inserted and removed laterally. A cartridge fixing mechanism 500 (FIGS. 13 to 15) of the first embodiment can also be installed on the stage rack 2300. On the contrary, in the first embodiment, a cartridge fixing mechanism (recessed groove part 113f and pin 113g) of FIG. 31 can also be provided instead of the cartridge fixing mechanism 500.

As shown in FIG. 22, one stage rack 2300 can preferably be provided with eight treatment lanes 2310 and eight tube accommodating parts 2318 so that eight different additional specimens are treated simultaneously. Corresponding thereto, one treatment executing unit 400 includes eight dispensation nozzles, and the eight dispensation nozzles can simultaneously move along each treatment lane and tube accommodating part and perform the pretreatment and the measurement processing in substantially the same protocol. Note that the numbers of treatment lanes 2310 and tube accommodating parts 2318 provided on the stage rack 2300 are not limited to eight, but a freely selected number, such as four, ten, 12, or 16, of treatment lanes can be provided. Similarly, the number of dispensation nozzles provided in the treatment executing unit 400 is not limited to eight, either, but a freely selected plural number, such as four, ten, 12, or 16, of dispensation nozzles can be provided corresponding to the number of lanes provided on the stage rack.

<Stage-Rack Transferring Mechanism>

Figure 24:
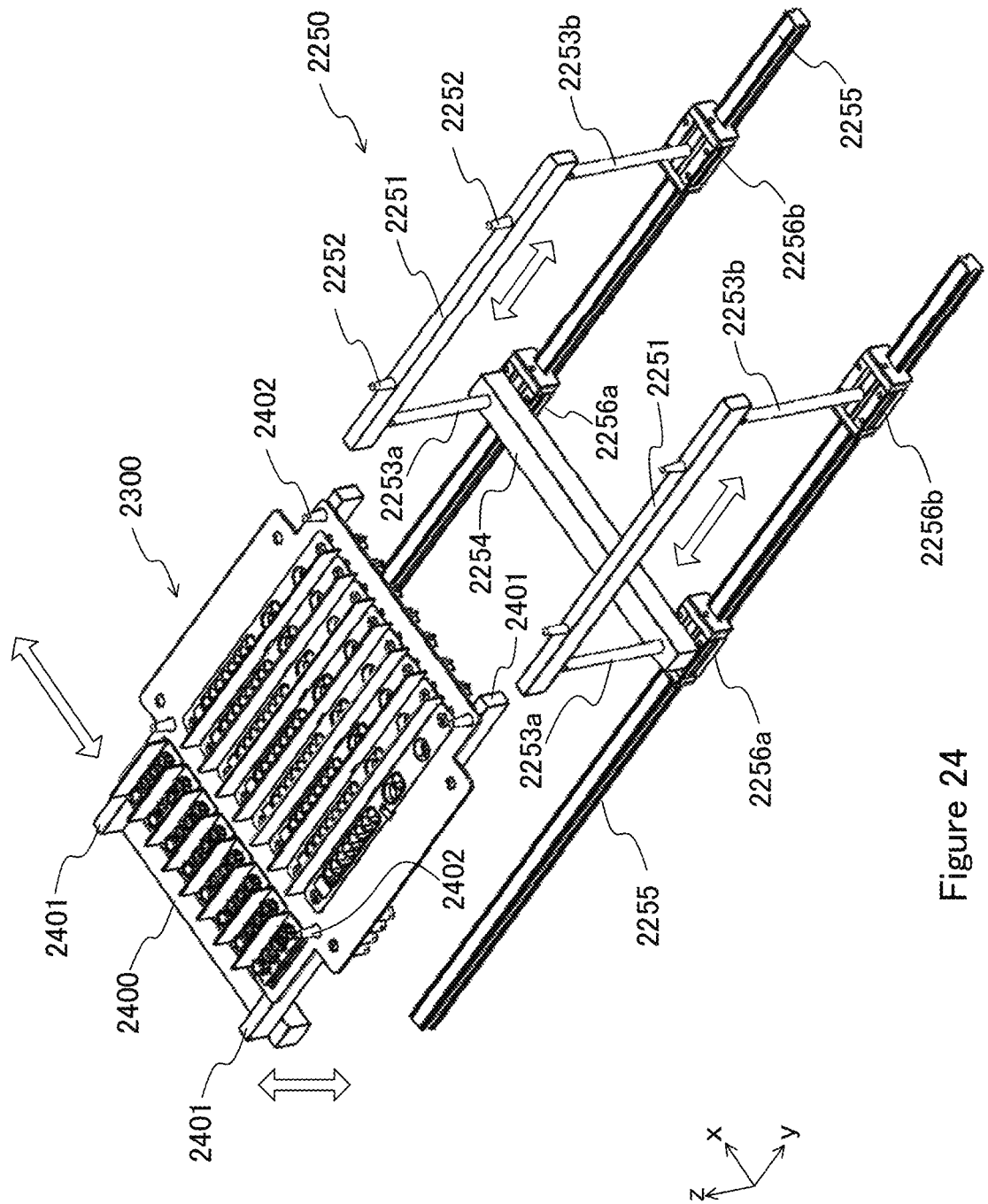
FIG. 24 is a perspective view of the stage rack and a stage rack mounting mechanism for use in the second embodiment of the present invention.
Figure 28:
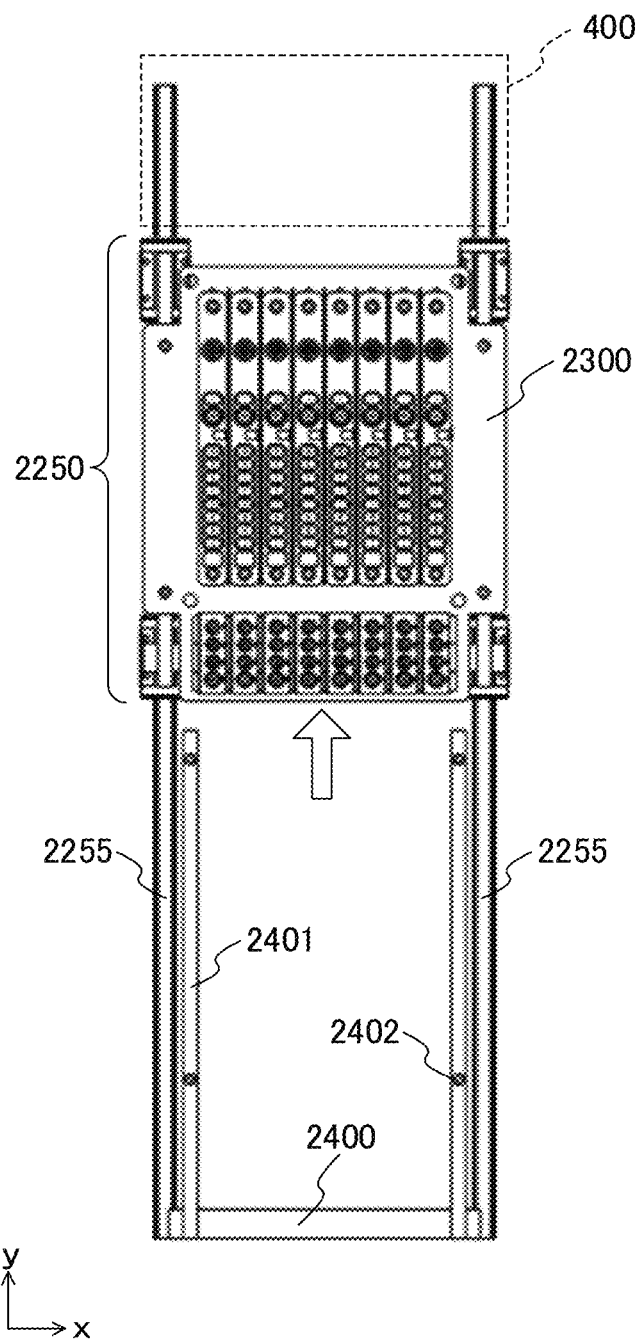
FIG. 28 is a plan view showing movement of the stage rack mounted on the stage rack mounting mechanism of FIG. 26.

As shown in FIG. 21, the stage-rack transferring mechanism 2400 includes a substantially U-shaped stage-rack transferring arm 2401. The stage-rack transferring arm 2401 is reciprocable by the motor for movement and the slider along the rail 2410 extending between the treatment preparation sub-system 2100 and the treatment execution sub-system 2200. The upper surface of each stage-rack transferring arm 2401 is provided with at least one transferring projection 2402 (FIGS. 24 and 28). When the transferring projection 2403 is inserted into the transferring connection hole 2314 of the stage rack 2300, the stage rack 2300 is fixed to the stage-rack transferring mechanism 2400 and then integrated therewith. Hence the stage rack 2300 becomes movable along the rail 2410 while being held by the stage-rack transferring arm 2401. The stage-rack transferring mechanism 2400 is thus liftable on the rail 2410 by a lifting mechanism, not shown, so as to insert or remove the transferring projection 2402 into or from the transferring connection hole 2314.

<Modification of Stage-Rack Mounting Mechanism>

In the present modification, instead of the stage-rack mounting mechanism 2220 shown in FIG. 21, the stage-rack mounting mechanism 2250 shown in FIG. 24 can be provided. The stage-rack mounting mechanism 2250 is provided on the treatment execution stage 2240 for each treatment executing unit 400. The stage-rack mounting mechanism 2250 is provided on the treatment execution stage 2240 and movable in the y-direction. The stage-rack mounting mechanism 2250 is made up of a pair of stage-rack mounting arms 2251, at least one projection 2252 provided in each of the stage-rack mounting arms 2251, a pair of first columns 2253a extending downward from the respective one ends of the stage-rack mounting arms 2251, a connection arm 2254 connecting the lower ends of the pair of first columns 2253a, a pair of first sliders 2256a provided at both ends of a connection arm 2254, second columns 2253b extending downward from the respective other ends of the stage-rack mounting arms 2251, and second sliders 2256b provided at the respective lower ends of the second columns 2253b. The stage 2240 is provided with a pair of rails 2255 so as to slide the first sliders 2256a and the second sliders 2256b in the y-direction. Further, the stage-rack mounting mechanism 2250 is provided with a motor for movement, not shown, for making the stage-rack mounting mechanism 2250 automatically movable.

Figure 25:
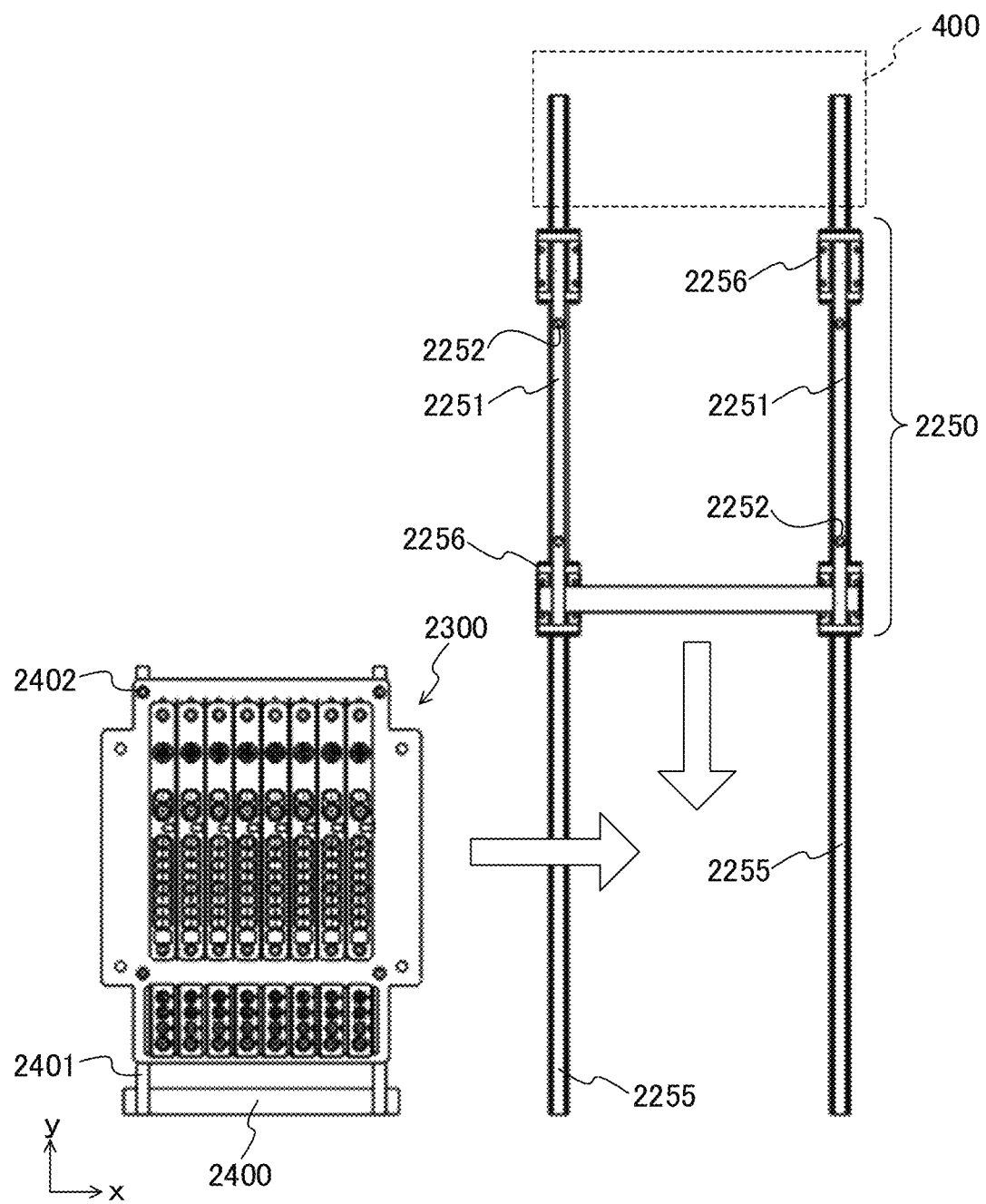
FIG. 25 is a plan view showing transfer of the stage rack to the stage rack mounting mechanism of FIG. 24.

Next, with reference to FIGS. 25 to 28, a description will be given of the transfer and mounting of the stage rack 2300 which are performed using the stage-rack transferring mechanism 2400 and the stage-rack mounting mechanism 2220. On the stage rack 2300, a consumable or the like is installed on each treatment lane at a consumable installed position of the treatment preparation sub-system 2100, while being held on the pair of stage-rack transferring arms 2401 of the stage-rack transferring mechanism 2400. Thereafter, as shown in FIG. 25, the stage rack 2300 moves from the treatment preparation sub-system 2100 to the treatment execution sub-system 2200. Further, the stage rack 2300 is transferred to above the treatment execution sub-system 2200 between the rails 2255, and the stage-rack mounting mechanism 2250 is moved to below the stage rack 2300, and the state becomes as shown in FIG. 26.

Figure 27:
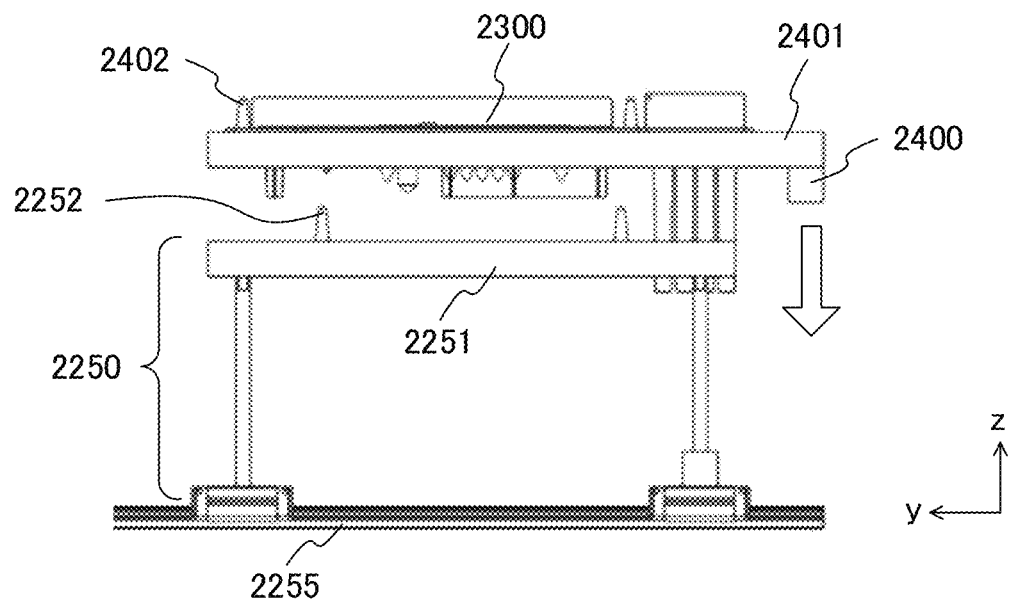
FIGS. 27(a) and 27(b) are side views showing mounting of the stage rack on the stage rack mounting mechanism of FIG. 26.
Figure 27:
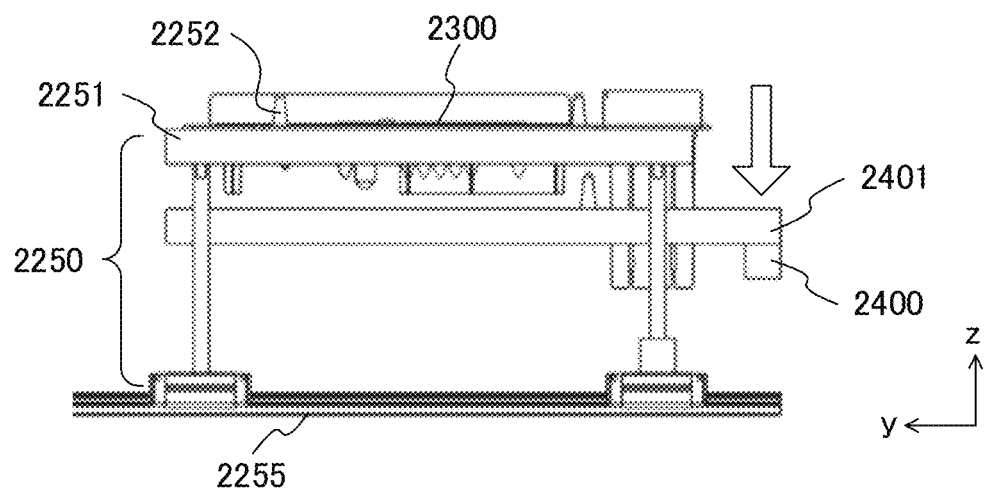

FIG. 27 is a side view of the state, shown in the top view of FIG. 26, as seen from the x-direction. In a state of FIG. 27(a), the stage-rack transferring mechanism 2400 holding the stage rack 2300 is located above the stage-rack mounting mechanism 2250. From the state of FIG. 27(a), when the stage-rack transferring mechanism 2400 is moved downward from the stage-rack mounting arms 2251 by a lifting mechanism, not shown, the state becomes as in FIG. 27(b). By this downward movement, the transferring projection 2402 of the stage-rack transferring arm 2401 comes off the transferring connection hole 2314 of the stage rack 2300, and the stage-rack mounting arms 2251 of the stage-rack mounting mechanism 2250 are inserted into the mounting connection hole 2316 of the stage rack 2300. Hence the stage rack 2300 is passed from the stage-rack transferring mechanism 2400 to the stage-rack mounting mechanism 2250. As shown in FIG. 26, a width $W_1$ between the outer surfaces of the pair of stage-rack transferring arms 2401 is smaller than a width $W_2$ between the inner surfaces of the pair of stage-rack mounting arms 2251, so that the stage rack 2300 and the stage-rack transferring arm 2401 do not interfere with each other at the time of the downward movement. After the state has become the state of FIG. 27(b), the stage-rack mounting mechanism 2250 holding the stage rack 2300 moves in the y-direction along the rail 2255 and then stops in the stage-rack mounting part (mounting position) in front of the treatment executing unit 400, to be located in a position where the treatment is possible, as shown in FIG. 28.

<Operation of Specimen Treatment and Measurement System>

For making a pretreatment step efficient and achieve high throughput, the specimen treatment and measurement system 2000 of the second embodiment is operated as follows. Firstly, preparation operation in the treatment preparation sub-system 2100 will be described. As shown in FIG. 21, the cartridges 112, 114 are pushed out onto the treatment preparation stage 2110 by using the cartridge push-out mechanism 2122. The pushed-out cartridges 112, 114 are installed on the stage rack 2300 by using the cartridge picker 2132.

Four each of the consumables such as the dispensation chip and the piercing chip stored in the consumable storing unit 2140 are picked up by quadruplet consumable pickers 2130a (FIG. 20) of the pickup unit 2130 and installed on the stage rack 2300. Each four consumables of the reagent container and/or the additional specimen container stored in the container storing part 2150 are also picked up by the quadruplet consumable pickers 2130a of the pickup unit 2130 and installed on the stage rack 2300 or the slide rack 2162.

Various reagents such as the PCR reagent stored in the reagent storing part 2152 are dispensed into the reagent container, installed on the stage rack 2300, by the dispensation nozzle 2130b of the pickup unit 2130. The main specimen stored in the main specimen tray 2160b of the main specimen storing part 2160 is dispensed into an additional specimen container 2320 installed on the stage rack 2300 or the additional specimen container of the slide rack 2162 by the dispensation nozzle 2130b of the pickup unit 2130. After the various consumables and the like are placed on the stage rack 2300, the consumables of the cartridges 114, 116 and the like are fixed onto the stage rack 2300 by the cartridge fixing mechanism. With the cartridge in the fixed state, the stage rack 2300 is transferred to the treatment execution sub-system 2200 by the stage-rack transferring mechanism 2400.

The stage rack 2300 transferred to the treatment execution sub-system is held by the pair of openable arms of the stage-rack mounting mechanism 2220, and mounted on the stage-rack mounting part 2210. In the state of being mounted on the stage-rack mounting part 2210, the stage rack 2300 is lowered by the lifting mechanism, and the PCR cartridge of the stage rack 2300 is caused to adhere to the heat block provided in the stage-rack mounting part 2210, to complete the mounting operation. When the mounting operation of the stage rack 2300 is completed, the treatment is executed in the treatment executing unit 400, or after the additional specimen and/or the PCR reagent and the like have been installed using the slide rack, the treatment is executed in the treatment executing unit 400. In the treatment step of the second embodiment, it is possible to execute steps S5 to S9 shown in the flowchart of FIG. 19 of the first embodiment.

The operation in the case of using the slide rack 2162 will be described. The slide rack 2162 is transferred to the treatment executing unit 400 immediately before the additional specimen and/or the PCR reagent and the like are used. Immediately before the use, an additional specimen is dispensed into a well or the tube (container) of the slide rack 2162 from the main specimen container, stored at a low temperature in the main specimen storing part 2160, by using the dispensation nozzle 2130b. Alternatively, a PCR reagent taken out from the PCR reagent container stored at a low temperature is dispensed into the well or the tube (container) of the slide rack 2162 by using the dispensation nozzle 2130b.

The slide rack 2162 is immediately transferred to the front (vicinity) of the treatment executing unit 400. The additional specimen or the PCR reagent transferred by the slide rack 2162 is sucked by the dispensation nozzle of the treatment executing unit 400 and appropriately dispensed into the well or the container of the stage rack 2300 mounted in the stage-rack mounting part 2210. The use of the slide rack 2162 keeps the reagent such as the PCR reagent and the specimen from being left on the non-cooled stage rack for a long time, so that it is possible to prevent deterioration in the reagent and the specimen.

Since the specimen treatment and measurement system 2000 of the second embodiment includes the plurality of treatment executing units 400, even when one treatment executing unit 400 is in operation, another treatment executing unit 400 can execute the pretreatment in parallel. In one treatment executing unit 400, the treatment (extraction, amplification, and measurement) is executed simultaneously on a plurality of (eight) treatment lines. When the treatment is ended, the stage-rack mounting mechanism 2220 removes the stage rack 2300 from the stage-rack mounting part 2210 and moves the stage rack 2300 to the stage-rack transferring mechanism 2400 to dispose of the consumable and the like, whereafter the next consumable and the like such as the cartridge is mounted and the treatment is repeated.

In the second embodiment, the number of treatment lines provided in each treatment executing unit 400 is not limited, and for example, any of four, six, eight, and twelve treatment lines can also be provided. Further, the three treatment executing units 400 have been provided in the second embodiment, but the number of treatment executing units 400 is not limited, and for example, five treatment executing units 400 can also be provided. In this case, a first group (three units) can be used for performing treatment of first to third common protocols, and a second group (two units) can be used for individual protocols or for urgent treatment. It is thereby possible as a whole system to perform treatment on various specimens in a random and continuous manner.

Types of specimens on which treatment can be performed in the first and second embodiments are, for example, whole blood, blood serum, blood plasma, urine, and the like. Pathogens with which an infectious disease due to a gene is diagnosed after pretreatment can, for example, be a human immunodeficiency virus (HIV), a hepatitis C virus, a tubercular bacillus, a chlamydia, and the like. The protocol of the treatment executed in the treatment executing unit 400 varies depending on test conditions such as the types of specimens or pathogens or test items. Accordingly, in the second embodiment, a plurality of common protocols corresponding to the types of specimens or pathogens are prepared. Specimens on which treatment can be performed in the same common protocol can be arrayed on the stage rack 2300 and treated on the same treatment stage 400 in accordance with the common protocol. For example, it is possible to collect specimens, on which treatment can be performed in a first common protocol, in a first treatment executing unit 400 and execute the treatment on the specimens, and it is possible to collect specimens, on which treatment can be performed in a second common protocol, in a second treatment executing unit 400 and execute the treatment on the specimens. As thus described, in the second embodiment, previously set test conditions are recognized, and specimens with the same protocol are collected, so that pretreatment can be performed thereon. The test condition can be read contactlessly from the information memory of a bar code or the like provided on each main specimen container by using the information reading part 2160c provided in the main specimen storing part 2160.

The operation for disposing of a consumable and the like on the stage rack 2300 will be described. Due to the possibility that a specimen to be treated contains a pathogen, care needs to be taken at the time of disposing of a consumable having come into contact with a specimen from the stage rack 2300 after completion of the treatment. In order for the user to dispose of, while not touching, a used consumable, a consumable except the cartridge is automatically picked up from the stage rack 2300 by using the dispensation nozzle of the treatment executing unit 400, and then disposed of into the consumable waste box 2230. As for a waste liquid containing a specimen (sample) in the state of being sucked by the dispensation chip mounted in the dispensation nozzle of the treatment executing unit 400 on the stage rack 2300, the dispensation nozzle of the treatment executing unit 400 is moved to above the waste liquid tank 2232, and thereafter the waste liquid is disposed of from the dispensation nozzle into the waste liquid tank 2232. Note that it is difficult to move the cartridges 114, 116 installed on the stage rack by using only one dispensation nozzle. Therefore, the stage rack 2300 after completion of the treatment is transferred to the consumable installed position of the treatment preparation sub-system 2100 by using the stage-rack mounting mechanism 2220 and the stage-rack transferring mechanism 2400, to release the fixing of the cartridge fixing mechanism. The cartridge is then taken out of the stage rack 2300 by using the cartridge picker 2132 and disposed of into the cartridge waste box 2170. Hence the stage rack 2300 comes into an empty state in which all consumables and the like have been removed from the stage rack 2300. In preparation for the next treatment, a required consumable and the like are installed on the stage rack 2300 in the empty state by using the pickup unit 2130 and the cartridge picker 2132.

As the treatment executing unit 400 used in the first and second embodiments, it is preferably possible to use "geneLEAD" supplied by Precision System Science Co., Ltd. The first and second embodiments make it possible to perform batch treatment from DNA extraction to real time PCR analysis. Especially the specimen treatment and measurement system 2000 of the second embodiment can execute the treatment in a high throughput and fully automated manner by combining specimen dispensation, reagent dispensation, and a consumable setting (loading) function in the plurality of treatment executing units 400. Further, it is possible to automatically perform batch management from dispensation from a main specimen to an additional specimen, dispensation of a reagent, to completion of pretreatment. In the specimen treatment and measurement system 2000 of the second embodiment, by combination of the treatment executing unit 400 including a plurality of dispensation nozzles (nozzle unit) arranged in parallel and the plurality of stage racks 2300, the random batch access treatment can be performed as a whole, and the pretreatment can be performed on 96 specimens per day. In the second embodiment (FIG. 21), the pretreatment has been performed by movement of the multiple string dispensation nozzles of the treatment executing unit 400 in the y-direction without movement of the stage rack 2300, mounted in the stage-rack mounting part 2210, in the y-direction, but this is not restrictive. For example, the treatment may be performed by movement of the stage rack 2300 in the x-direction without movement of the multiple string dispensation nozzles of the treatment executing unit 400 in the y-direction.

A description will be given of a case where the specimen treatment and measurement system 2000 of the second embodiment is taken as a DNA treatment system. In this case, the stage rack 2300 includes a DNA extraction etc. functioning part that extracts and/or refines DNA and a DNA amplification functioning part that amplifies DNA in specified positions on each treatment lane. In the treatment preparation sub-system 2100, a plurality of consumables such as a container, a cartridge, a dispensation chip, a piercing chip, and/or a sealing cap, which are used in each functioning part, are arranged in advance in positions of each functioning part on each lane of the stage rack 2300.

In the second embodiment, each consumable can be automatically placed or installed on the stage rack 2300, and with the stage rack 2300 in the state of being mounted on the stage-rack mounting part 2210, the treatment executing unit 400 can automatically execute DNA extraction, DNA amplification, and measurement of the amplified DNA. Further, after the treatment has been executed, the used consumable can be automatically disposed of from the stage rack 2300, to make the stage rack reusable. In the DNA extraction functioning part, by attraction and separation (magtration technology) of a magnet to and from the dispensation chip of the treatment executing unit 400, it is possible to automatically execute extraction of DNA adsorbed to a magnetic particle in a solution held in the dispensation chip.

Since the specimen treatment and measurement system of the second embodiment includes the plurality of treatment executing units 400, even when treatment is being carried out in one treatment executing unit 400, the stage rack 2300 can be mounted in another empty treatment executing unit 400 not in operation at freely selected timing so that the treatment can be performed continuously. Therefore, the specimen treatment and measurement system of the second embodiment as a whole can achieve the random batch access system.

In the specimen treatment and measurement system of the first or second embodiment, the consumable can preferably include at least one of a well, a tube, a dispensation chip, a piercing chip, and a cap of the well. In the specimen treatment and measurement system of the first or second embodiment, at least a part of the cartridge can preferably include at least one prefilled well in which an extracted reagent of the nucleic acid and/or an amplified reagent of the nucleic acid is sealed in advance. In the specimen treatment and measurement system of the first or second embodiment, at least a part of the cartridge can preferably include a prefilled cartridge for an extracted reagent in which the extracted reagent of the nucleic acid is sealed in advance, and a prefilled cartridge for an amplified reagent in which an amplified reagent of the nucleic acid is sealed in advance.

In the specimen treatment and measurement system of the first or second embodiment, the cartridge can preferably be provided with at least one or a plurality of a well for a reagent, a well for extracting nucleic acid, a well for amplifying nucleic acid, a cap holding part that holds a cap of the well, and a dispensation chip holding part that holds a dispensation chip. In the specimen treatment and measurement system of the first or second embodiment, preferably, the treatment lane can be provided with a tube that accommodates a micro particle for detecting nucleic acid, a plurality of the micro particles, to each of which a material capable of being specifically coupled to a different specimen is fixed, are arranged at known positions in the tube, and the specimen treatment and measurement system can be provided with a detector that detects a signal issued by the micro particle in the tube.

In the specimen treatment and measurement system of the first or second embodiment, preferably, each treatment lane can be provided with an electrophoresis chip that performs electrophoresis of the specimen, and the specimen treatment and measurement system can be provided with a detector that detects a band separated from the specimen in the electrophoresis chip. In the specimen treatment and measurement system of the first or second embodiment, it is preferably possible to provide a biochemical testing device that conducts one or a plurality of biochemical tests on a plurality of specimens. The biochemical tests include at least one of a dog C-reactive protein (CRP) (inflammation marker), serum amyloid protein (SAA), total bile acids (TBA), fibrin degradation product (FDP), lipase, and D-dimer.

The invention claimed is:

1. A specimen treatment and measurement system for executing treatment in parallel which is made up of extraction of nucleic acid contained in each of a plurality of specimens, amplification of the extracted nucleic acid, and measurement of the amplified nucleic acid, the system comprising:
a cartridge storing unit that stores one type or a plurality of types of cartridges for use in the treatment corresponding to the plurality of specimens, the one type or the plurality of types of cartridges including at least cartridges configured for amplifying and measuring nucleic acid;
a specimen treatment part including a plurality of treatment lanes configured to execute the treatment in parallel, each of the cartridges configured for amplifying and measuring nucleic acid being installed on each of the plurality of treatment lanes;
a specimen storing unit that stores each of the plurality of specimens;
a plurality of dispensation nozzles corresponding to the plurality of treatment lanes and configured to move moving up and down in a unified manner;
a cartridge transferring unit configured to transfer that transfers the plurality of cartridges for amplifying and measuring nucleic acid to the plurality of lanes, respectively;
a specimen transferring unit configured to transfer the plurality of specimens to the plurality of treatment lanes; and a
controller programmed to control the transfer of the cartridge for amplifying and measuring nucleic acid by the cartridge transferring unit and the transfer of the plurality of specimens by the specimen transferring unit, wherein the controller is programmed to use the cartridge transferring unit to transfer to each of the plurality of treatment lanes the cartridge for amplifying and measuring nucleic acid corresponding to each of the plurality of specimens, the controller further is programmed to use the specimen transferring unit to transfer the plurality of specimens to the plurality of treatment lanes, and the controller is programmed to execute at least the amplification of the extracted nucleic acid, and the measurement of the amplified nucleic acid in parallel by using the plurality of dispensation nozzles on each of the cartridges for amplifying and measuring nucleic acid which are installed on each of the plurality of treatment lanes.

2. The specimen treatment and measurement system according to claim 1, wherein the treatment and/or the measurement is batch treatment that is simultaneously performed on the plurality of specimens.

3. The specimen treatment and measurement system according to claim 1, comprising a specimen treatment preparing unit obtained by integrating the cartridge transferring unit and the specimen transferring unit.

4. The specimen treatment and measurement system according to claim 1, wherein at least a part of the cartridge includes a prefilled well in which a reagent and/or a solution required for the treatment is sealed in advance.

5. The specimen treatment and measurement system according to claim 1, wherein the plurality of specimens are classified into a plurality of groups among which common treatment operation is possible, and the controller selects a plurality of specimens, included in the same group, from the plurality of specimens and executes the treatment in parallel.

6. The specimen treatment and measurement system according to claim 5, wherein the treatment is executed in parallel on the plurality of specimens for each group altogether to perform treatment on a whole of the plurality of specimens in a continuous manner.

7. The specimen treatment and measurement system according to claim 1, wherein the cartridge transferring mechanism includes a cartridge picker that adsorbs the at least one cartridge.

8. The specimen treatment and measurement system according to claim 7, wherein the cartridge picker vacuum-sucks the cartridge.

9. The specimen treatment and measurement system according to claim 7, wherein the cartridge picker includes a protrusion, and the cartridge includes a recess into which the protrusion is inserted.

10. The specimen treatment and measurement system according to claim 7, wherein the cartridge picker adsorbs both ends of the cartridge.

11. The specimen treatment and measurement system according to claim 7, wherein the cartridge transferring mechanism includes a cartridge-picker lifting mechanism that lifts and lowers the cartridge picker.

12. The specimen treatment and measurement system according to claim 7 wherein the specimen treatment and measurement system includes a consumable storing unit that stores a consumable for use in the plurality of lanes, and the cartridge transferring mechanism includes a consumable picker that takes the consumable out of the consumable storing unit.

13. The specimen treatment and measurement system according to claim 12, wherein the cartridge transferring mechanism includes a consumable-picker lifting mechanism that lifts and lowers the consumable picker.

14. The specimen treatment and measurement system according to claim 7, wherein the cartridge includes a cartridge information recording part in which cartridge information is recorded, and the cartridge transferring mechanism includes an information reading part that reads the cartridge information out of the cartridge information memory.

15. The specimen treatment and measurement system according to claim 1, wherein a first cartridge and a second cartridge are installed on each of the plurality of treatment lanes, and the controller removes the second cartridge with the treatment on the specimen terminated from the plurality of treatment lanes by using the cartridge transferring mechanism, while treatment is performed on the specimen in the first cartridge.

16. The specimen treatment and measurement system according to claim 1, wherein the specimen container includes a specimen information recording part in which specimen information and/or reagent information for use in treatment on the specimen is recorded, and the specimen transferring unit or the specimen storing unit includes an information reading part that reads the specimen information and/or the reagent information out of the specimen information memory.

17. The specimen treatment and measurement system according to claim 1, wherein the specimen storing unit includes a specimen conveying mechanism that circularly conveys the plurality of specimens, and a specimen takeout position for taking the specimen out of the specimen conveying mechanism.

18. The specimen treatment and measurement system according to claim 1, wherein the specimen storing unit includes a temperature adjusting mechanism for preventing degeneration or deterioration of the plurality of specimens.

19. The specimen treatment and measurement system according to claim 1, comprising a cartridge fixing mechanism that fixes the cartridge to the specimen treatment part.

20. The specimen treatment and measurement system according to claim 1, wherein the cartridge fixing mechanism includes a first claw and a second claw that push both ends of the cartridge.

21. The specimen treatment and measurement system according to claim 1, comprising a treatment executing unit that includes a plurality of dispensation nozzles so as to execute the treatment in parallel on the cartridge installed in each of the plurality of treatment lanes.

22. The specimen treatment and measurement system according to claim 1, comprising a measurement unit for executing the measurement of the plurality of specimens.

* * * * *